United States Patent
Berry et al.

(10) Patent No.: US 12,233,061 B2
(45) Date of Patent: Feb. 25, 2025

(54) MICROVASCULAR ANGINA

(71) Applicants: THE UNIVERSITY COURT OF THE UNIVERSITY OF GLASGOW, Strathclyde (GB); CAMBRIDGE ENTERPRISE LIMITED, Cambridgeshire (GB)

(72) Inventors: Colin Berry, Strathclyde (GB); Thomas J. Ford, Strathclyde (GB); Anthony P. Davenport, Cambridgeshire (GB)

(73) Assignees: THE UNIVERSITY COURT OF THE UNIVERSITY OF GLASGOW, Strathclyde (GB); CAMBRIDGE ENTERPRISE LIMITED, Cambridgeshire (GB)

( * ) Notice: Subject to any disclaimer, the term of this patent is extended or adjusted under 35 U.S.C. 154(b) by 862 days.

(21) Appl. No.: 17/430,453

(22) PCT Filed: Feb. 12, 2020

(86) PCT No.: PCT/EP2020/053560
§ 371 (c)(1),
(2) Date: Aug. 12, 2021

(87) PCT Pub. No.: WO2020/165226
PCT Pub. Date: Aug. 20, 2020

(65) Prior Publication Data
US 2022/0184067 A1    Jun. 16, 2022

(30) Foreign Application Priority Data

Feb. 12, 2019  (GB) ........................ 1901913
Jan. 24, 2020  (GB) ........................ 2001040

(51) Int. Cl.
*A61K 31/497*    (2006.01)
*A61P 9/10*      (2006.01)

(52) U.S. Cl.
CPC .............. *A61K 31/497* (2013.01); *A61P 9/10* (2018.01)

(58) Field of Classification Search
CPC .................................................. A61K 31/497
See application file for complete search history.

(56) References Cited

U.S. PATENT DOCUMENTS

2008/0058642 A1    3/2008    Gould

FOREIGN PATENT DOCUMENTS

| WO | 9640681 A1   | 12/1996 |
|----|--------------|---------|
| WO | 2004018044 A2| 3/2004  |
| WO | 2006056760 A1| 6/2006  |
| WO | 2009068906 A2| 6/2009  |

OTHER PUBLICATIONS

Notice of reasons for refusal, JP patent application No. 2021-546770, Jan. 23, 2020 (8 pages).
Spieker et al., Endothelin Receptor Antagonists in Congestive Heart Failure: A New Therapeutic Principle for the Future J. Am. Coll. Cardiol., 37 (6), 1493-1505 (2001).
Ford et al., Stratified Medical Therapy Using Invasive Coronary Function Testing in Angina The CorMicA Trial, Cardiology, 72 (23), 2841-2855 (2018).
Anon, The anti-anginal effect of Zibotentan in the Coronary Slow Flow Phenomenon, ANZCTR, 1-6, Jan. 11, 2018.
Alvarez et al., Coronary Slow-Flow Phenomenon as an Under-recognized and Treatable Source of Chest Pain: Case Series and Literature Review, J. Invest. med. High Impact Case Rep., 6, 1-5 (2018).
Reriani et al., Long-Term Administration of Endothelin Receptor Antagonist Improves Coronary Endothelial Function in Patients With Early Atherosclerosis, Circulation, 122 (10), 958-966 (2010).
Liou et al., Design and Rationale for the Endothelin-1 Receptor Antagonism in the Prevention of Microvascular Injury in Patients with non-ST Elevation Acute Coronary Syndrome Undergoing Percutaneous Coronary Intervention (ENDORA-PCI) Trial, Cardiovasc. Drugs Ther., 30 (2), 169-175 (2016).
Schelman et al., A phase I study of zibotentan (ZD4054) in patients with metastatic, castrate-resistant, prostate cancer, Invest. New Drugs, 29 (1), 118-125 (2009).
Gupta et al., A Genetic Variant Associated with Five Vascular Diseases is a Distal Regulator of Endothelin-1 Gene Expression, Cell, 170 (3), 522-533.e15 (2017).
Ford et al., Genetic dysregulation of endothelin-1 is implicated in coronary microvascular dysfunction Eur. Heart J., ehz915, 1-14, Jan. 23, 2020.
Claudio et al., Why names matter for women: MINOCA/INOCA (myocardial infarction/ischemia and no obstructive coronary artery disease), Clin. Cardiol., 41 (2), 185-193 (2018).
International Search Report and Written Opinion issued in PCT/EP2020/053560, mailed Jul. 14, 2020.
Search Report under Section 17 issued in GB1901913.2, mailed Jun. 26, 2019.

*Primary Examiner* — Golam M Shameem
(74) *Attorney, Agent, or Firm* — Meunier Carlin & Curfman LLC

(57) ABSTRACT

The invention provides means of diagnosing and treating microvascular angina (MVA). Diagnostic applications of intra-coronary guidewires are provided. Treatment of MVA patients with zibotentan is disclosed. The MVA patient can be identified and selected for treatment via the diagnostic applications provided.

8 Claims, 17 Drawing Sheets

FIGURE 10
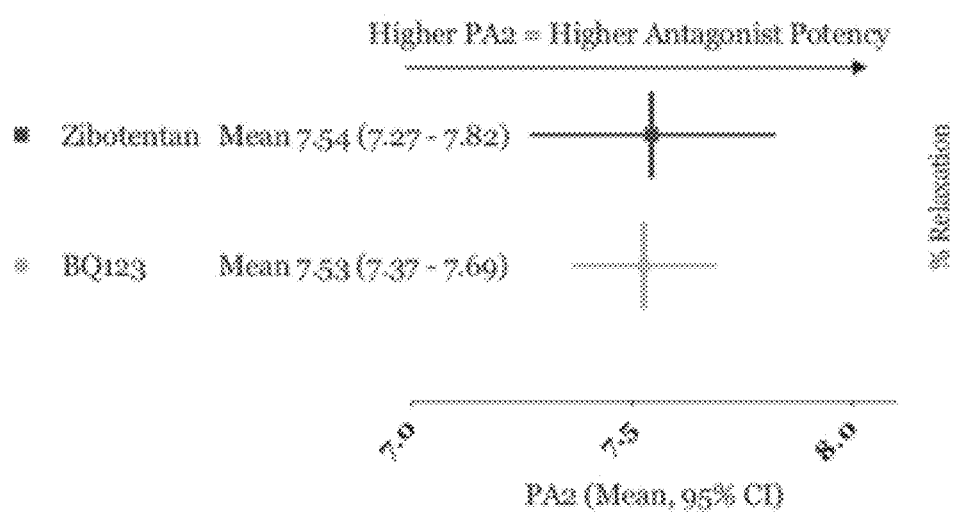
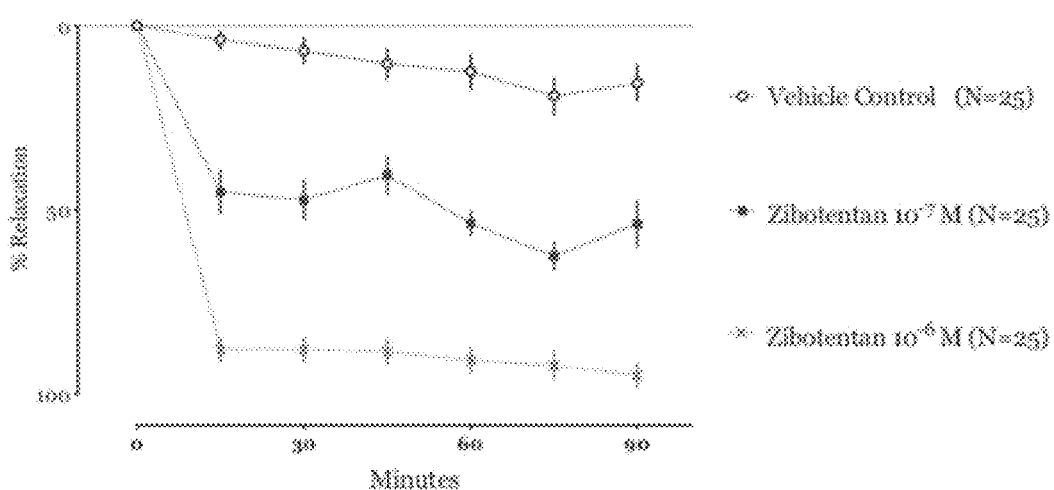

MICROVASCULAR ANGINA

FIELD OF THE INVENTION

The present invention relates to methods and compositions that are useful in the diagnosis and treatment of angina with non-obstructive coronary artery disease, and in particular, the diagnosis and treatment of microvascular angina (MVA).

BACKGROUND OF THE INVENTION

Cardiovascular disease (CVD) is the leading cause of mortality worldwide.[1] Angina is a common presentation of CVD often described as chest discomfort/pain caused by insufficient blood supply to the heart muscle (ischaemia). Annually in the UK, there are over 20,000 new cases of angina with substantial associated morbidity and healthcare resource utilisation.[2] The diagnosis can be made from the history alone, although some medical professionals consider the detection of obstructive lesions (blockages) in the large and visible coronary arteries to be a prerequisite. This is a common misconception, however; angina is not synonymous with obstructive coronary artery disease (CAD).

Ischaemia is common in patients without obstructive coronary artery disease (INOCA, which stands for "ischaemia and no obstructive CAD").[3] The criteria for definitive diagnosis of microvascular angina in INOCA subjects has been revised to include evidence of coronary microvascular dysfunction as well as evidence of ischaemia.[4] INOCA may be due to vasospasm of the larger coronary arteries and/or their branches, including the microvessels. INOCA may also be due to a supply:demand mismatch whereby the vasodilator capacity of the coronary circulation (large and/or small vessels) is insufficient to meet demand. Finally, INOCA may be due to an increase in vascular resistance to blood flow, such as secondary to rarefaction of small vessels and/or vessel remodelling.

Coronary microvascular dysfunction portends a poor prognosis regardless of the presence of obstructive coronary lesions (FIG. 1).[5,6] It may result from vascular disease processes in the microcirculation including atherosclerosis, vessel remodelling and rarefaction. When studied systematically, CMD affects approximately three quarters of angina patients with a negative angiogram.[7] Importantly, these subjects are often overlooked or remain without a clear diagnosis despite an increased risk of death and cardiovascular events.[8-10]

The present inventors have explained that the 'stenosis centric' approach to the diagnosis of coronary artery disease (CAD) neglects the broader pathophysiology of angina and disorders of coronary artery function (Ford et al, EHJ, 2017). That paper describes four distinct disease states, which can be termed 'coronary endotypes': (1) diffuse epicardial and microvascular disease, including focal epicardial stenosis, in which FFR (fractional flow reserve) and CFR (coronary flow reserve) are both reduced and in which IMR (index of microvascular resistance) is increased; (2) focal epicardial stenosis (with preserved microvascular function) in which FFR (fractional flow reserve) and IMR (index of microvascular resistance) are both reduced and in which CFR (coronary flow reserve) is increased; (3) isolated microvascular disease, a cause of microvascular angina in which FFR (fractional flow reserve) is normal (FFR>0.80), in which CFR (coronary flow reserve) is reduced and in which IMR (index of microvascular resistance) is greatly increased; and (4) diffuse epicardial and microvascular disease in which FFR (fractional flow reserve) is reduced (FFR<=0.80) and IMR (index of microvascular resistance) is increased and in which CFR (coronary flow reserve) is reduced.

Certain non-invasive methods such as perfusion MRI and cardiac magnetic resonance (CMR) are known for assessing chest discomfort/pain and coronary artery disease in general. First line non-invasive methods are presented in the UK National Institute for Health and Care Excellence (NICE) clinical guidance notice on the assessment and diagnosis of "chest pain of recent onset" (originally published 24 Mar. 2010), which recommends a 12-lead electrocardiogram (ECG) in patients with suspected or confirmed "acute coronary syndrome", which covers a range of conditions including unstable angina, ST-segment-elevation myocardial infarction (STEMI) and non-ST-segment-elevation myocardial infarction (NSTEMI). In patients where stable angina is indicated by clinical assessment or the ECG, the NICE guidance notice recommends a computed tomography (CT) coronary angiogram. In May 2018, Hsu et al published methods of quantifying myocardial blood flow (MBF) from contrast-enhanced CMR perfusion imaging and quantitative coronary angiography (QCA).[11] However, the Hsu et al acknowledged that these methods might not reflect microvascular disease in patients.

While arteriography (angiogram) can identify obstructive CAD and while treatments such as stents and bypass surgery are available to treat obstructive CAD patients, there is no widely available definitive test that is specific for diagnosing microvascular angina. When a patient suffering from chest pain tests negative by coronary angiography, the physician cannot readily determine whether the pain is due to non-cardiac causes or whether the patient has a form of INOCA such as microvascular angina. Thus, diagnosis is suboptimal and 50% of treated patients re-attend hospital after treatment and have a twofold increased risk of cardiovascular related death and/or myocardial infarction. Most treatments for microvascular angina relieve pain or alleviate acute symptoms but do not address the underlying condition in the long term.

ETR Antagonists and Vascular Function

Endothelin (ET-1) is a peptide hormone released by endothelial cells which is a potent vasoconstrictor, and which binds the endothelin A receptor ($ET_AR$) and the endothelin B receptor ($ET_BR$). Several endothelin receptor antagonists have been studied with respect to their effects on vascular function. Papadogeorgos et al (2009) studied the effects of the selective $ET_AR$ antagonist BQ123 and the dual $ET_AR/ET_BR$ antagonist bosentan on coronary microvascular function in type 2 diabetes patients. BQ123 is a selective $ET_AR$ antagonist while bosentan blocks both $ET_AR$ and $ET_BR$. Tschudi et al (1994) showed that the selective $ET_AR$ antagonist FR139317 was less effective than the dual $ET_AR/ET_BR$ antagonist bosentan at blocking ET-1 induced contractions of human mammary resistance arteries, harvested from human patients undergoing bypass surgery. Newby et al (1998) showed that BQ123 causes a similar degree of vasodilation in 'syndrome X' patients and control subjects. Johnson et al (2013) showed that $ET_AR$ antagonist darusentan increases flow homogeneity in subjects with low myocardial perfusion homogeneity. Reriani et al (2010) showed that 6 months of treatment with the $ET_AR$ antagonist atrasentan improves coronary microvascular endothelial function in patients with coronary microvascular endothelial dysfunction.

Zibotentan is a highly specific $ET_AR$ antagonist (Maguire & Davenport, 2014). Beltrame et al are investigating the anti-anginal effect of Zibotentan (ANZCTR 2018) in subjects the coronary slow flow phenomenon (CSFP). The European Society of Cardiology defines CSFP as an angiographic phenomenon characterised by the slow passage of contrast in the absence of obstructive coronary artery disease (TIMI frame count >25). CSFP is thus an angiographically derived proxy which is not invasively validated but is considered one subtype of coronary microvascular dysfunction. Acute coronary syndrome (myocardial infarction) is a common presentation of CSFP which is often noted in patients without microvascular angina (e.g. coronary artery ectasia, valvular heart disease or heart failure).[12] Overall, most microvascular angina patients do not have CSFP[12] and many patients with CSFP do not have microvascular angina. The efficacy of zibotentan on CSFP patients is not yet known.

Endothelin Dysregulation in Patients with INOCA

ET-1 is implicated in the pathophysiology of microvascular angina. Kaski et al observed that this group of patients had increased plasma ET-1 with increased coronary vascular resistance with resultant inverse relationship with coronary blood flow.[13] Higher circulating ET-1 has been described in this group by other researchers[14]. ET-1 mediates its effects on vascular tone via endothelin-A receptors ($ET_AR$) and endothelin-B receptors ($ET_BR$)[15]. $ET_AR$ activation mediates vasoconstriction via direct action on vascular smooth muscle cells (VSMCs). The effects of $ET_BR$ are more varied, however in healthy endothelium the $ET_BR$ activation counteracts $ET_AR$ mediated vasoconstriction. In disease states with endothelial impairment (microvascular angina), the clinical effects of $ET_BR$ modulation are not clear.

Evidence Supporting the Use of Selective ETR Antagonists in Patients with INOCA

In a randomised, placebo-controlled trial of the oral $ET_AR$ antagonist ($ET_A$-RA) atrasentan (10 mg PO daily) administered for 6 months in 47 patients, Reriani et al observed that chronic $ET_A$-RA therapy improved coronary microvascular endothelial function as revealed by IC-ACh.[16] Evidence was also drawn from a randomised double-blind trial of sitaxentan (a highly selective $ET_AR$ antagonist).[17] Patients with heart failure and preserved ejection fraction (HFpEF), treated with sitaxentan, had an increase in exercise time compared to placebo without adverse cardiovascular events seen with less selective endothelin receptor antagonists (ERAs) (e.g. fluid retention). Sitaxsentan was withdrawn from development owing to hepatotoxicity however this trial lends support to the strategy of selective $ET_AR$ antagonists for patients with CMD.

Zibotentan (N-(3-Methoxy-5-methylpyrazin-2-yl)-2-[4-(1,3,4-oxadiazol-2-yl)phenyl]pyridine-3-sulfonamide) is a compound developed by Astra-Zeneca for treatment of metastatic prostate cancer but was discontinued due to futility in a phase III trial. Zibotentan is an endothelin receptor antagonist that is highly selective for $ET_AR$ over $ET_BR$ (by a factor of around $10^7$)[18].

SUMMARY OF THE INVENTION

The present inventors have developed an invasive method of detecting microvascular angina, which using an interventional diagnostic procedure (IDP) using a dual-sensor diagnostic guidewire and intra-coronary infusions of acetylcholine. This method is also used to refine and validate non-invasive methods that were previously unable to provide a reliable indication of microvascular angina. The inventors consider the small vessel disease in the heart to be part of a systemic problem and have demonstrated the efficacy of zibotentan in the context of INOCA in the microvascular angina disease state for the first time, in the small vessels of patients confirmed to have microvascular angina.

Accordingly, in a first aspect, the invention provides zibotentan for use in a method of treating angina in a patient with INOCA, the method comprising administering the zibotentan to the patient. In a related aspect, the invention provides a method of treating angina in a patient with INOCA, the method comprising administering the zibotentan to the patient. In some embodiments, the INOCA is microvascular angina.

In some embodiments, the patient has been selected for treatment by measuring the index of microvascular resistance (IMR), coronary flow reserve (CFR), resistance reserve ratio (RRR) and/or acetylcholine (ACh) vasoreactivity in the heart of the patient, using a diagnostic guidewire as described herein. These measurements can be made combination with the use of pharmacological probes. The pharmacological probe may be adenosine, which may be administered by intravenous infusion via a large peripheral vein. The diagnostic guidewire is preferably a pressure-temperature sensitive guidewire. The guidewire may be placed into the distal third of a major epicardial coronary artery, for instance the left anterior descending (LAD). In other instances, the left circumflex or right coronary artery (RCA) may be used. CFR measurement may involve the calculation of myocardial Fractional Flow Reserve (FFR), which can be calculated by the ratio of mean distal coronary pressure to mean aortic pressure at maximal hyperemia. The patient may be selected for treatment when IMR is measured to be greater than 25, and/or when CFR is measured to be less than 2.0. In some embodiments, the patient may be selected for treatment following measurement of the hyperaemic microvascular resistance (HMR) of over 2.5. HMR may be measured using a Doppler wire. These methods may be used to quantify and/or diagnose the presence of coronary microvascular dysfunction in the heart of the patient, e.g. to identify INOCA and/or MVA.

In some embodiments, the patient may be selected for treatment following a CFR measurement of less than 2.0 using positron emission tomography (PET scan) and/or stress perfusion MRI. This may be with assessment of myocardial perfusion reserve ratio or absolute pixel wise assessment of myocardial blood flow. These methods may be used to quantify and/or diagnose the presence of coronary microvascular dysfunction in the heart of the patient, e.g. to identify INOCA and/or MVA.

In some embodiments, the patient may be selected for treatment following the detection of the presence or absence of a single nucleotide polymorphism at locus rs9349379 in the genome of the patient. The patient may be selected for treatment if the rs9349379 locus is homozygous or heterozygous for the G allele.

In some embodiments, the patient may be selected for treatment following a combination of two or more of the diagnostic guidewire, Doppler wire, PET scan, perfusion MRI and or SNP related methods described herein.

The efficacy of the treatment can be confirmed by testing. In some embodiments the mean exercise duration of the patient, measured on a standardised treadmill test, is increased following treatment. In some embodiments, the severity of the angina is reduced such that the angina is considered to fall in a lower class on the CCS angina grading scale.

Typically the medical treatments and medical uses of zibotentan disclosed herein involve the administration of more than one dose of the zibotentan, wherein the doses of zibotentan are administered at different time points. In preferred embodiments, the method comprises administering the zibotentan to the patient at a dosage of 10 mg every day (10 mg daily). In other embodiments, the dosage may be doubled (20 mg daily) or halved (5 mg daily). In further embodiments, even lower dosages may be used (less than 5 mg daily, e.g. 2 mg daily or 1 mg daily). In further embodiments, even higher dosages may be used (more than 20 mg daily, e.g. 25 mg daily or 50 mg daily). The zibotentan can in some embodiments be administered at a dose selected from a range of doses, defined at its end-points by any of the single dose values disclosed herein. In some embodiments, the zibotentan can be administered at a dose selected from the dose values disclosed herein every other day. In other embodiments, the zibotentan can be administered at a dose selected from the dose values disclosed herein every week.

In other aspects, the invention provides method of diagnosing microvascular angina in a subject by inserting a guidewire into the coronary artery of the subject, the guidewire having proximal and distal pressure sensors; positioning the guidewire such that the proximal pressure sensor is located in the coronary artery and the distal pressure sensor is located in a coronary microvessel; the method comprising measuring the fractional flow reserve (FFR) and the coronary flow reserve (CFR), and calculating the index of microvascular resistance (IMR); wherein the subject is diagnosed with microvascular angina if the IMR>25. In a related aspect, the invention provides a guidewire for use in a method of diagnosing microvascular angina in a subject, the method comprising inserting the guidewire into the coronary artery of the subject, the guidewire having two pressure sensors; positioning the guidewire such that the proximal pressure sensor is located in the coronary artery and the distal pressure sensor is located in a coronary microvessel, the method comprising measuring the fractional flow reserve (FFR) and the coronary flow reserve (CFR), and calculating the index of microvascular resistance (IMR); wherein the subject is diagnosed with microvascular angina if the IMR>25. The guidewire is disposable, i.e. it is 'single-use'.

The diagnostic guidewire is preferably a pressure-temperature sensitive guidewire. The guidewire may be placed into the distal third of a major epicardial coronary artery, for instance the left anterior descending (LAD). In other instances, the left circumflex or right coronary artery (RCA) may be used. CFR measurement may involve the calculation of myocardial Fractional Flow Reserve (FFR), which can be calculated by the ratio of mean distal coronary pressure to mean aortic pressure at maximal hyperemia.

In some embodiments, acetylcholine (ACh) is infused into the coronary lumen, either through a microcatheter or through a guide catheter associated with the guidewire, to provoke a spasm in the coronary microvessels. This diagnosis of microvascular spasm (a subtype of coronary microvascular dysfunction) is made when there is reproduction of ischaemic chest symptoms, ST segment deviation on the ECG but luminal constriction of <90% of the epicardial coronary artery (as per the COVADIS working group definition). The ACh may be administered at incrementally increasing concentrations over a range of about $10^{-6}$M infusion up to 100 mcg IC bolus. In some embodiments, ACh is administered at concentrations of about 0.2 µg/mL, about 2 µg/mL and then about 20 µg/mL.

In some embodiments, an intravenous infusion of adenosine is administered via a large peripheral vein to induce steady-state maximal hyperemia prior to the insertion of the guidewire. In some embodiments, the adenosine is infused at a rate of 100-200 µg·kg$^{-1}$·min$^{-1}$, e.g. at 140 µg·kg$^{-1}$·min$^{-1}$.

In some embodiments, the diagnostic methods further comprise the steps of infusing glyceryl trinitrate (GTN) and then measuring coronary endothelial-independent function.

In some embodiments, the diagnostic methods may include performing a positron emission tomography (PET scan) and/or stress perfusion MRI on the patient and then measuring CFR of less than 2.0 from the PET and/or MRI data as described herein. This may be with assessment of myocardial perfusion reserve ratio or absolute pixel wise assessment of myocardial blood flow.

In some embodiments, the diagnostic methods may include the detection of the presence or absence of a single nucleotide polymorphism at locus rs9349379 in the genome of the patient. The patient may be diagnosed with an INOCA if (e.g. in addition to other diagnostic data, such as those data obtained using the other methods described herein) the rs9349379 locus is homozygous or heterozygous for the G allele.

SUMMARY OF THE FIGURES

FIG. 10 shows that zibotentan antagonises constrictor responses to ET-1 with pK$_B$ of 7.54 (N=8), comparable to that of BQ123 (panel A). Panel B shows that zibotentan produces a concentration-dependent inhibition of an established constrictor response to ET-1 (P<0.001).

DETAILED DESCRIPTION OF THE INVENTION

Figure 1:
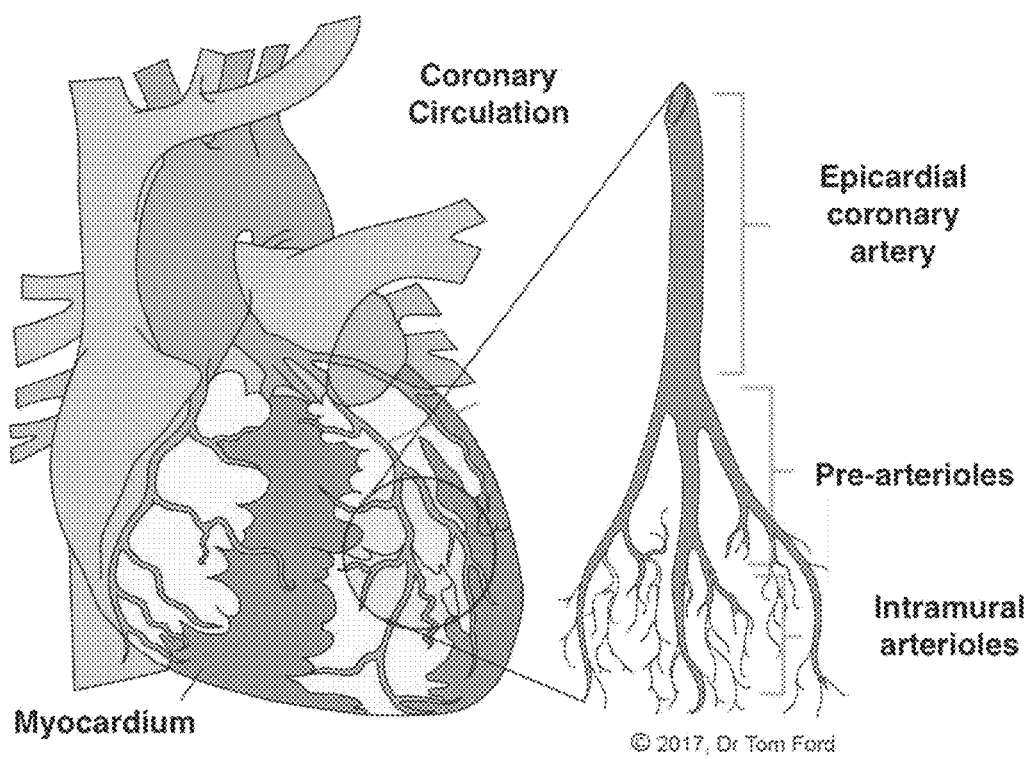
FIG. 1 is a schematic representation of the coronary artery (right hand side) shown in context of the myocardium (left).
Figure 2:
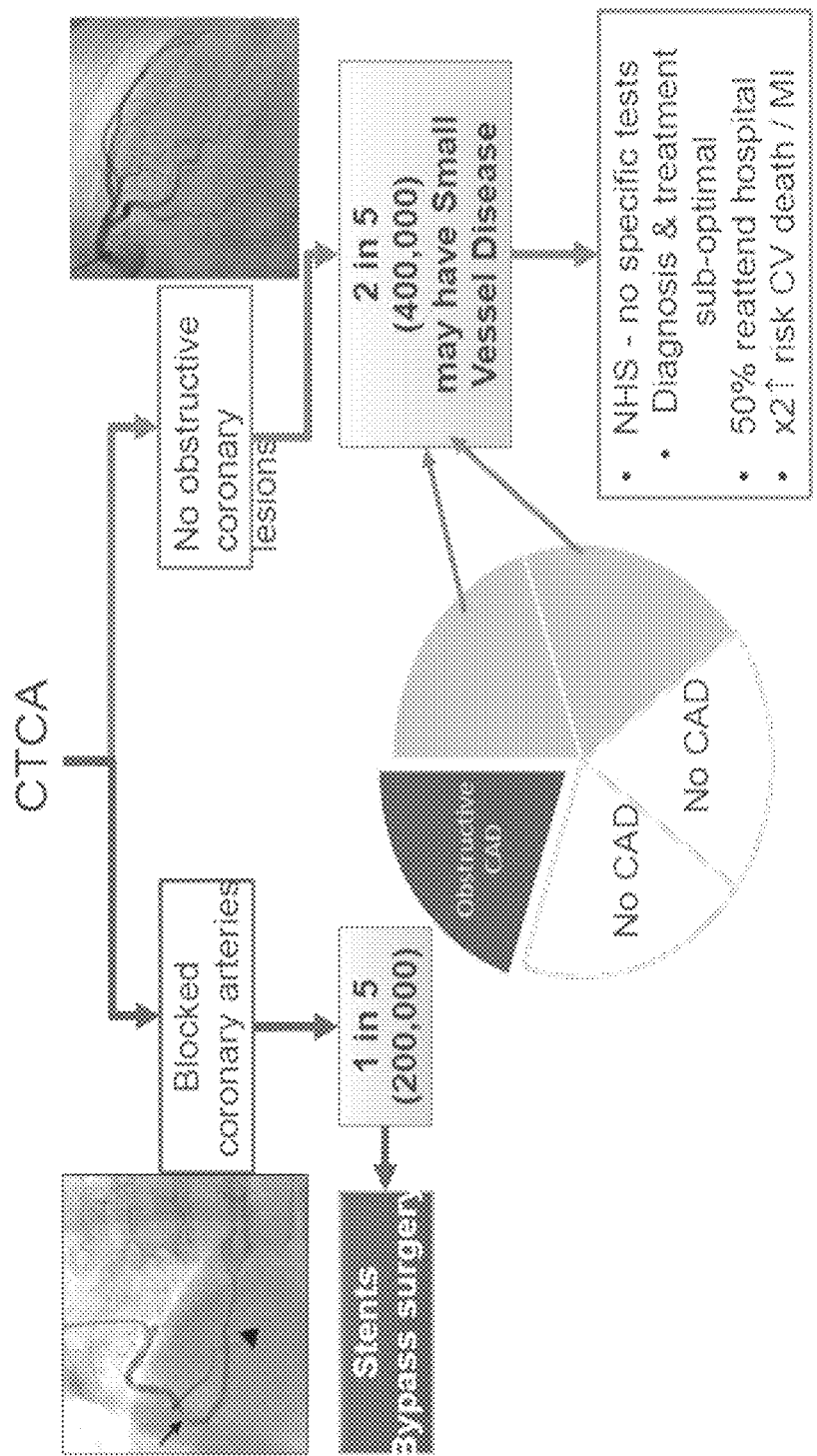
FIG. 2 is a flow diagram showing the proportional outcomes for patients presenting with chest pains following computed tomography coronary angiography (CTCA) scan.

Aspects and embodiments of the present invention will now be discussed with reference to the accompanying figures. Further aspects and embodiments will be apparent to those skilled in the art. All documents mentioned in this text are incorporated herein by reference.

Definitions

The "subject" to be treated may be any animal or human. The subject is preferably mammalian, more preferably human. The subject may be a non-human mammal, but is more preferably human. The subject may be male or female. The subject may be a patient. Therapeutic uses may be in human or animals (veterinary use).

Medicaments and pharmaceutical compositions according to aspects of the present invention may be formulated for administration by a number of routes, including but not limited to, parenteral, intravenous, intra-arterial, intramuscular, intratumoural, oral and nasal. Preferably, the medicament or pharmaceutical composition is prepared for oral administration. The medicaments and compositions may be formulated in fluid or solid form. Fluid formulations may be formulated for administration by injection to a selected region of the human or animal body. Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Pharmaceutical compositions may be prepared using a pharmaceutically acceptable "carrier" composed of materials that are considered safe and effective. "Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In some embodiments, this term refers to molecular entities and compositions approved by a regulatory agency of the US federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

The term "carrier" refers to diluents, binders, lubricants and disintegrants. Those with skill in the art are familiar with such pharmaceutical carriers and methods of compounding pharmaceutical compositions using such carriers.

The pharmaceutical compositions provided herein may include one or more excipients, e.g., solvents, solubility enhancers, suspending agents, buffering agents, isotonicity agents, antioxidants or antimicrobial preservatives. When used, the excipients of the compositions will not adversely affect the stability, bioavailability, safety, and/or efficacy of the active ingredient, i.e. zibotentan, used in the composition. Thus, the skilled person will appreciate that compositions are provided wherein there is no incompatibility between any of the components of the dosage form. Excipients may be selected from the group consisting of buffering agents, solubilizing agents, tonicity agents, chelating agents, antioxidants, antimicrobial agents, and preservatives.

It may be convenient or desirable to prepare, purify, and/or handle a corresponding salt of the active compound, zibotentan, for example, a pharmaceutically-acceptable salt of zibotentan. Such zibotentan salts are encompassed as part of the invention, insofar as they are for use in the methods defined by the claims. Examples of pharmaceutically acceptable salts are discussed in Berge et al., 1977, "Pharmaceutically Acceptable Salts," J. Pharm. Sci., Vol. 66, pp. 1-19.

We use an interventional diagnostic procedure that combined guidewire-based direct measurement of coronary vascular function followed by pharmacological vasoreactivity testing. Specifically, the procedure included a guidewire-based measurement of coronary vascular function (fractional flow reserve [FFR], coronary flow reserve [CFR], and the index of microvascular resistance [IMR]) followed by pharmacological vasoreactivity testing with acetylcholine (ACh) and glyceryl trinitrate (GTN) and has been previously described.[7,19]

In brief, an intravenous infusion of adenosine (140 µg·kg$^{-1}$·min$^{-1}$) was administered via a large peripheral vein to induce steady-state maximal hyperemia. A pressure-temperature sensitive guidewire was placed into the distal third of a major epicardial coronary artery (typically the left anterior descending (LAD)). The myocardial FFR was calculated by the ratio of mean distal coronary pressure to mean aortic pressure at maximal hyperemia. A FFR≤0.80 was taken as abnormal and indicative of flow-limiting coronary artery disease.[20] CFR was calculated using thermodilution as resting mean transit time divided by hyperemic mean transit time.[21] A CFR<2.0 was defined as abnormal representing impaired vasodilator reserve. The IMR was calculated as the product of mean hyperemic transit time and mean distal coronary pressure at hyperaemia.[22] An IMR>25 was defined as abnormal and indicative of increased microvascular resistance. These invasive parameters were simultaneously derived in real-time using dedicated software (Coroventis, Uppsala, Sweden).

Grading the Severity of Angina

The severity of angina may be measured via medical examination. Common grading systems such as the Canadian Cardiovascular Society grading of angina pectoris (sometimes referred to as the CCS angina grading scale) may be used. The CCS angina grading scale of angina is presented as follows:

Class 0—Asymptomatic Angina. This is described as "mild myocardial ischemia with no symptoms."

Class 1—Angina only with strenuous exertion. This is described as "the presence of angina during strenuous, rapid, or prolonged ordinary activity (walking or climbing the stairs)."

Class 2—Angina with moderate exertion. This is described as "slight limitation of ordinary activities when they are performed rapidly, after meals, in cold, in wind, under emotional stress, during the first few hours after waking up, but also walking uphill, climbing more than one flight of ordinary stairs at a normal pace and in normal conditions."

Class 3—Angina with mild exertion. This is described as "having difficulties walking one or two blocks or climbing one flight of stairs at normal pace and conditions."

Class 4—Angina at rest. This is described as "no exertion needed to trigger angina."

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

EXAMPLES

Example 1: Use of the Novel Quidewire of the Invention for Diagnosing MVA

Figure 3:
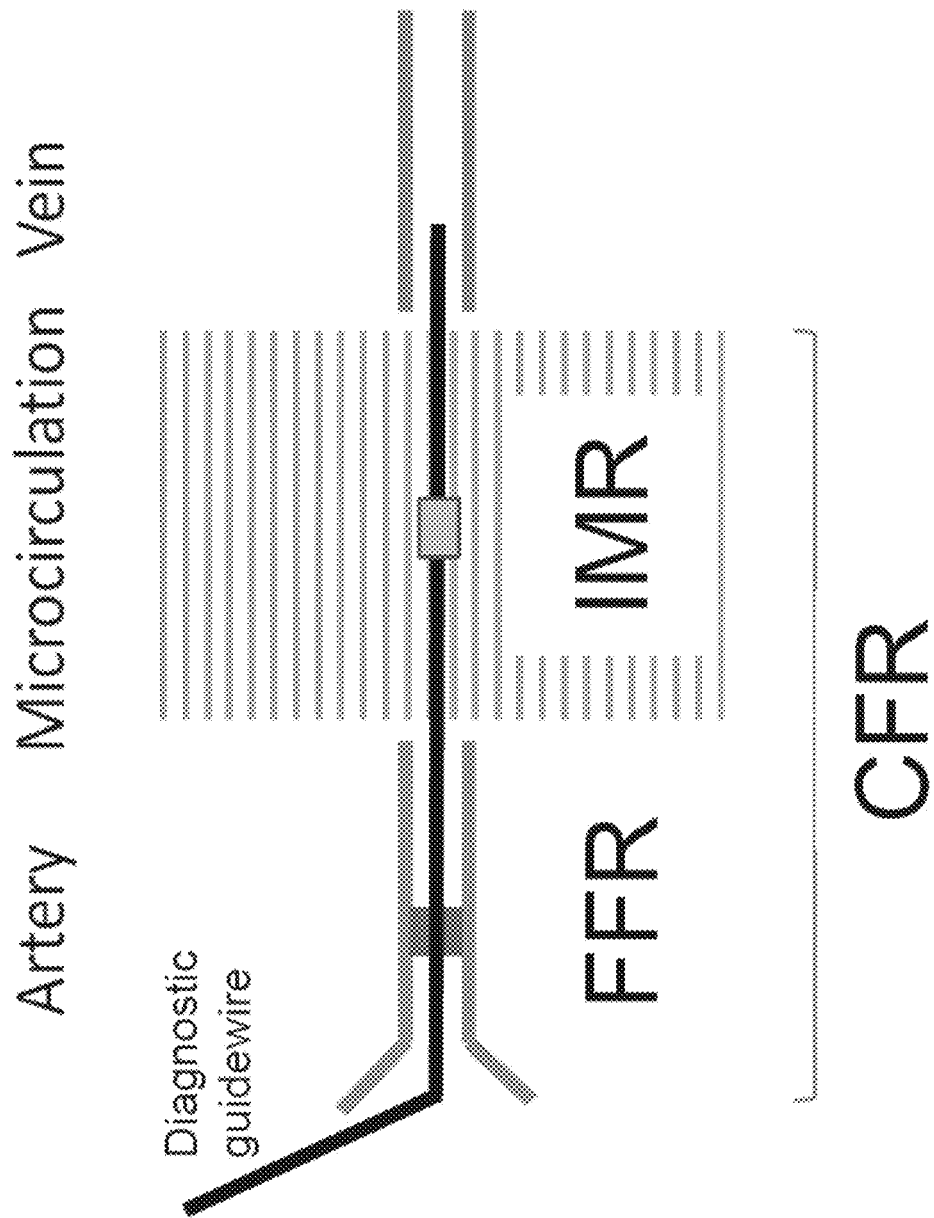
FIG. 3 is a schematic representation of the dual-sensor diagnostic guidewire of the invention, in situ in the coronary artery and microvessels. (CFR, coronary flow reserve; FFR, fractional flow reserve; IMR, index of microvascular resistance.)

Measurement of Coronary Vascular Function In Vivo (Shown in FIG. 3)

We use an interventional diagnostic procedure that combines guidewire-based direct measurement of coronary vascular function followed by pharmacological vasoreactivity testing. Specifically, the procedure includes a guidewire-based measurement of coronary vascular function (fractional flow reserve [FFR], coronary flow reserve [CFR], and the index of microvascular resistance [IMR]) followed by pharmacological vasoreactivity testing with acetylcholine (ACh) and glyceryl trinitrate (GTN) and has been previously described in other clinical settings.[7,19]

In brief, an intravenous infusion of adenosine (140 µg·kg$^{-1}$·min$^{-1}$) is administered via a large peripheral vein to induce steady-state maximal hyperemia. A pressure-temperature sensitive guidewire is placed into the distal third of a major epicardial coronary artery (typically the left anterior descending (LAD)). The myocardial FFR is calculated by the ratio of mean distal coronary pressure to mean aortic pressure at maximal hyperemia. A FFR≤0.80 is taken as abnormal and indicative of flow-limiting coronary artery disease.[20] CFR is calculated using thermodilution as resting mean transit time divided by hyperemic mean transit time.[21] A CFR<2.0 is defined as abnormal representing impaired vasodilator reserve. The IMR is calculated as the product of mean hyperemic transit time and mean distal coronary pressure at hyperaemia.[22] An IMR>25 is defined as abnormal and indicative of increased microvascular resistance. These invasive parameters are simultaneously derived in real-time using dedicated software (Coroventis, Uppsala, Sweden).

Coronary Vasoreactivity Testing

The target vessel is the LAD coronary artery. If technical factors, e.g. vessel tortuosity, preclude assessment of this artery then the left circumflex or right coronary artery (RCA) is selected. We assess endothelium-dependent coronary vasomotor function using intra-coronary infusions of ACh via the guiding catheter at concentrations of 0.182, 1.82, and 18.2 µg/mL ($10^{-6}$, $10^{-5}$, and $10^{-4}$ mol/L, respectively) at 1 mL/min for 2 minutes via a mechanical infusion pump.[23] We then immediately perform provocation testing for epicardial coronary artery spasm using a 100 μg bolus of ACh (5.5 mL of $10^{-4}$ mol/L over 20 seconds—reduced to 50 μg for the RCA). In order to assess non-endothelial dependent vasodilatation, 300 μg of GTN is administered by manual intra-coronary bolus injection.

Example 2: Evidence for the Role of ET-1 on Vasoconstriction in MVA Patients (Ford et al; EHJ 2018).[24]

Aims: Coronary microvascular dysfunction and/or vasospasm are potential causes of ischemia in patients with no obstructive coronary artery disease. We tested the hypothesis that these patients also have functional abnormalities in peripheral small arteries.

Methods and results: Patients were prospectively enrolled and categorized as having microvascular angina (MVA), vasospastic angina (VSA) or normal control based on coronary artery function tests incorporating probes of endothelial and endothelial-independent function (acetylcholine and adenosine), described above in Example 1. Gluteal biopsies of subcutaneous fat were performed in 81 subjects (62 years, 69% female, 59 MVA, 11 VSA, and 11 controls). Resistance arteries were dissected enabling study using wire myography.

Maximum relaxation to ACh was reduced in MVA vs. controls median [77.6 vs. 98.7%; 95% confidence interval (CI) of difference 2.3-38%; P=0.0047]. Endothelium-independent relaxation [sodium nitroprusside (SNP)] was similar between all groups. The maximum contractile response to endothelin-1 (ET-1) was greater in MVA (median 121%) vs. controls (100%, 95% CI 4.7-45%, P=0.015). Response to the thromboxane agonist, U46619, was also greater in MVA (median 143%) vs. controls (109%; 95% CI 13-57%, P=0.003). Patients with VSA had similar abnormal patterns of peripheral vascular reactivity including reduced maximum relaxation to ACh (median 79.0% vs. 98%; P=0.03) and increased response to constrictor agonists including ET-1 (125% vs. 100%; P=0.02). In all groups, resistance arteries were around 50-fold more sensitive to the constrictor effects of ET-1 compared with U46619.

Conclusions: Systemic microvascular abnormalities are common in patients with MVA and VSA. These mechanisms may involve ET-1 and were characterized by enhanced vasoconstriction and endothelial dysfunction.

The results are shown in Table 1:

TABLE 1

Maximum responses and sensitivities to dilator and constrictor agonists in resistance arteries from patients with microvascular angina (MVA), vasospastic angina (VSA) and control subjects with normal coronary function.

|  |  | MVA (n = 59) |  | VSA (n = 11) |  | Control (n = 11) |
| --- | --- | --- | --- | --- | --- | --- |
| Normalised Vessel Diameter in μm (±SD)[†] |  | 345 (±95) | P-value* 0.34 | 332 (±85) | P-value* 0.66 | 315 (±96) |
| ACh | N | 48 |  | 9 |  | 10 |
|  | $E_{max(\%)}$ | 77.6 | <0.01 | 79.0 | 0.03 | 98.7 |
|  | $pIC_{50}$ | 7.1 | 0.49 | 7.1 | 0.73 | 7.3 |
| SNP | N | 49 |  | 10 |  | 10 |
|  | $E_{max(\%)}$ | 97 | 0.99 | 99 | 0.99 | 98 |
|  | $pIC_{50}$ | 7.0 | 0.50 | 6.5 | 0.30 | 7.5 |
| ET-1 | N | 54 |  | 11 |  | 9 |
|  | $E_{max(\%)}$ | 121 | 0.03 | 125 | 0.02 | 100 |
|  | $pEC_{50}$ | 9.6 | 0.17 | 9.5 | 0.49 | 9.3 |
| U44619 | N | 54 |  | 10 |  | 11 |
|  | $E_{max(\%)}$ | 143 | 0.01 | 141 | 0.04 | 109 |
|  | $pEC_{50}$ | 8.0 | 0.02 | 7.5 | 0.67 | 7.50 |

ACh: Acetylcholine. SNP: sodium nitroprusside.
$E_{max}$: maximum efficacy for constrictor agonists is expressed in terms of percentage of maximum response to KPSS solution, for dilator agonists $E_{max}$ refers to maximum relaxation after preconstruction with U46619. Potency is expressed as the −log concentration required to produce 50% of the maximum response ($IC_{50}$ for antagonists, $EC_{50}$ for agonists).
[†]$L_o$ = 90% of the normalised vessel diameter (Data for diameter is mean (SD)).
All other values are median value with P-values denoting two tailed comparison of medians with control group.
The Kruskal-Wallis test was used to evaluate this with an adjustment for multiple comparisons (controlling the false discovery rate).
*Efficacy and potency were not significantly different between MVA and VSA groups for any of the agonists studied.

Figure 6:
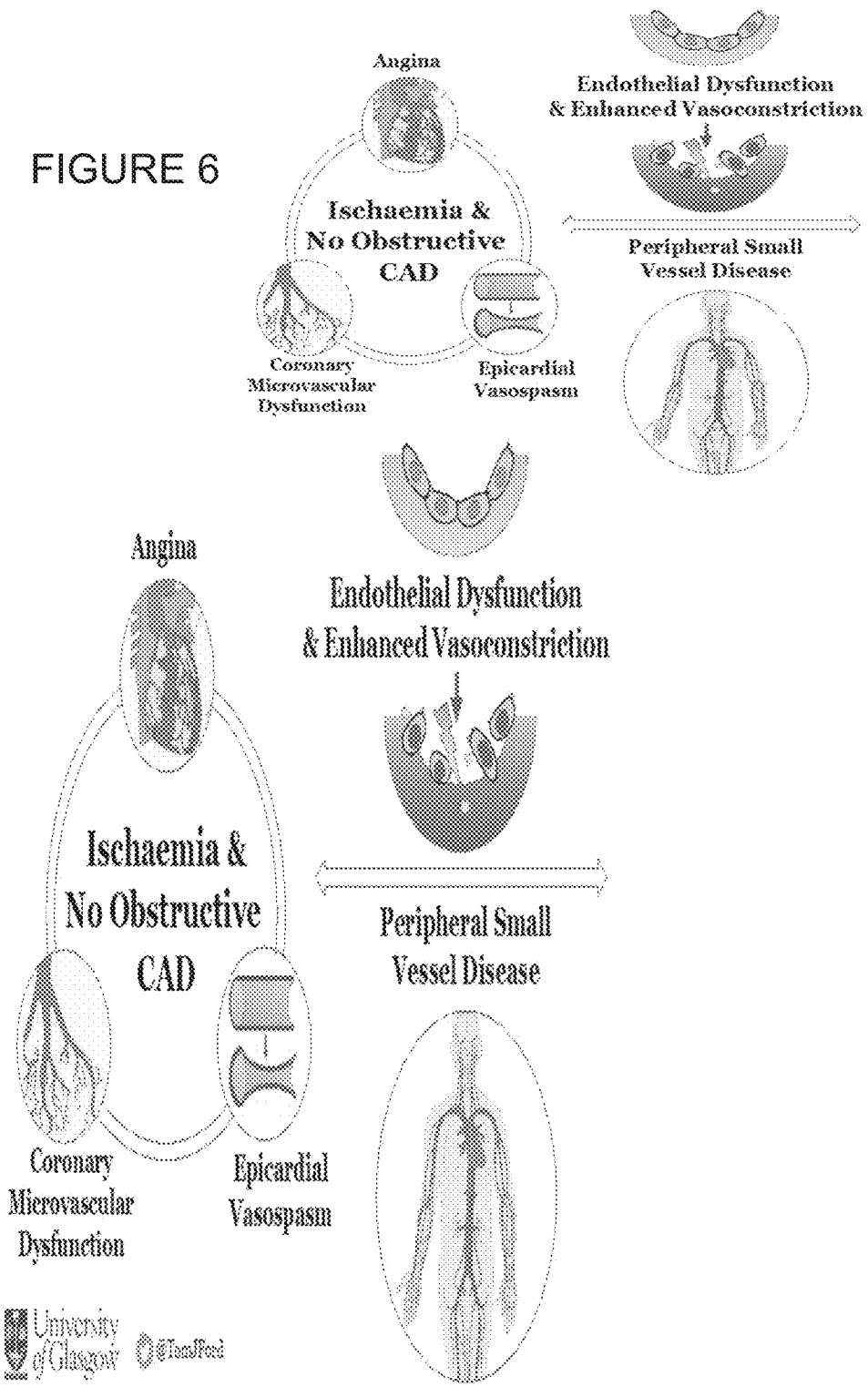
FIG. 6 Systemic microvascular dysfunction in microvascular and vasospastic angina, showing increased susceptibility of the microvessels of INOCA patients to ET-1 mediated vasoconstriction, compared with the microvessels of control subjects.

These results confirm endothelial dysfunction and enhanced vasoconstriction in peripheral arterioles of patients with MVA compared to controls and indicate the ET-1 pathway as a potential therapeutic target. (FIG. 6—Central Illustration—ET-1 increased constriction and reduced endothelial function in microvascular angina).

Example 3: The Effect of Zibotentan on the Peripheral Arteries of Microvascular Angina Patients Hypothesis: In patients with MVA, zibotentan is a more potent inhibitor of the ET-1 vascular response than BQ123, a selective ETA receptor antagonist (ERA), and BQ788, a selective ETBR antagonist.

Aim: We used peripheral resistance arteries isolated from patients with MVA and matched controls to investigate whether the ultra-selective ETAR antagonist, Zibotentan, is a more potent inhibitor of the ET-1 vascular response ex vivo than BQ123 in patients with MVA. NB. BQ-123 is not effective orally. It is used as a pharmacological tool to study ERA function.

Figure 4:
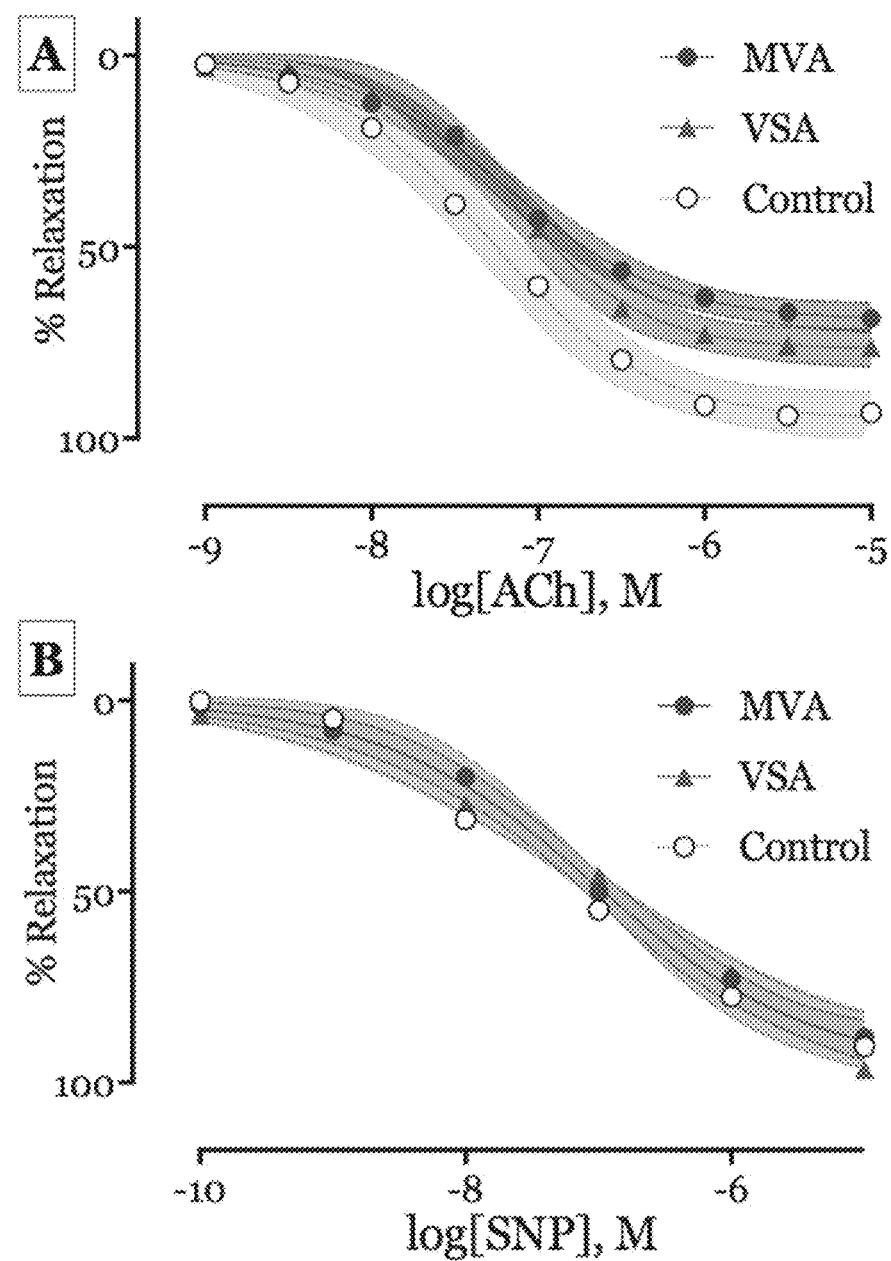
FIG. 4 shows the dilation of microvessels in response to acetyl choline (ACh; panel A) and sodium nitroprusside (SNP; panel B) in MVA patients and control subjects. ACh and SNP evoked concentration-dependent relaxations in arteries precontracted with the thromboxane agonist, U46619, from both MVA patients and control subjects. There is a highly significant reduction in relaxation to ACh in the subjects with MVA versus control but no difference in relaxation to SNP. These findings suggest that peripheral endothelial impairment is present in MVA subjects.
Figure 5:
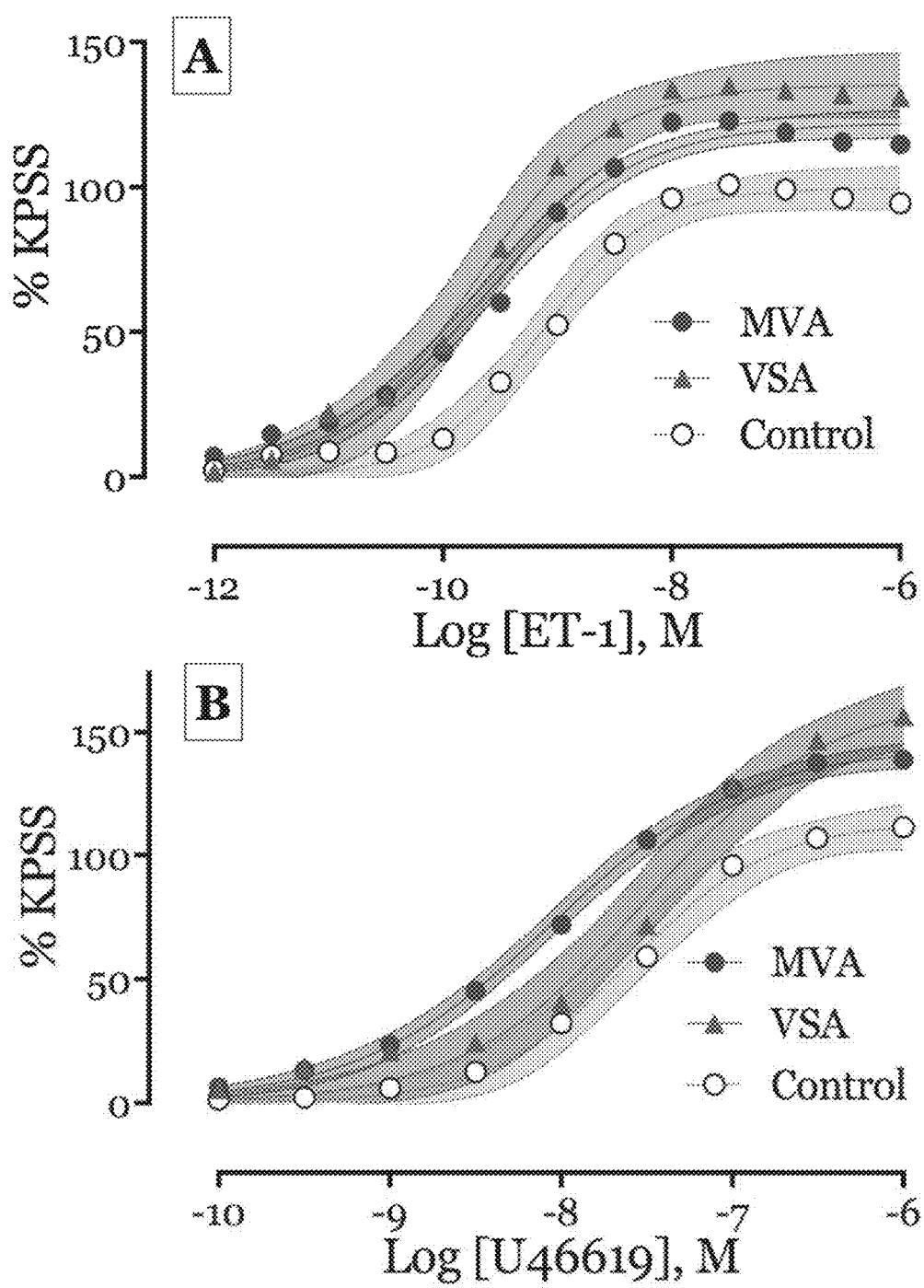
FIG. 5 shows the contraction of microvessels in response to ET-1 (panel A) and U46619 (panel B) in MVA patients and control subjects. All arteries responded in a concentration-dependent manner to both ET-1 and U46619 and the response is presented as the percentage of the potassium induced response (KPSS). The maximum constrictor responses to ET-1 are significantly greater in MVA patients than in control subjects and the maximum constrictor responses to U46619 are significantly greater in patients compared to control subjects. The increase is statistically highly significant (p<0.001).
Figure 7:
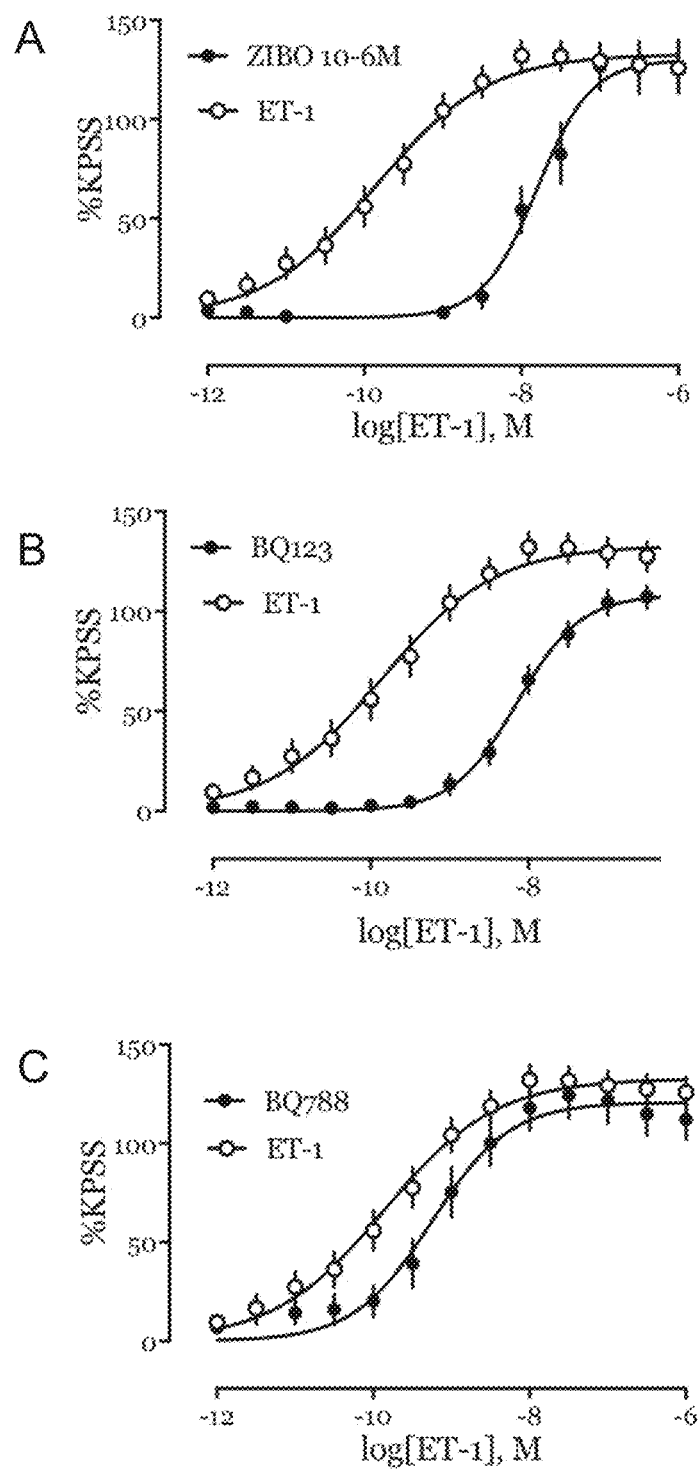
FIG. 7 Determinants of ET-1 response using ex vivo pharmacological studies modulating Endothelin receptors ($ET_AR$ & $ET_BR$). Vasoconstriction was induced with ET-1 at the concentration shown on the x axis. The microvessels were pre-treated with various antagonists as shown. A—Zibotentan (Selective $ET_AR$ antagonist) potently inhibits the ET-1 mediated vessel constriction (curve shifts to the right). B—The peptide BQ123 also inhibits the ET-1 response however BQ123 is not a bioavailable compound and has reduced selectivity compared with Zibotentan. C shows that ET$_B$R antagonism with high dose BQ788 produces only minimal shift in the ET-1 response. Together this data supports that the ET$_A$R is the dominant effector of the ET-1 mediated vascular response in MVA.

Results: Cumulative concentration response curves (CCRCs) were performed in freshly isolated, paired arterioles after preincubation with BQ788 and BQ123, 10-6M (n=31 subjects) or zibotentan, 10-6M (n=8). The potency of ET-1 induced vasoconstriction in the presence of the ETAR antagonist, zibotentan, is markedly reduced in patients with MVA (FIG. 4). ETB receptor antagonism with BQ788 had negligible effect on the ET-1 constrictor response, whereas an effect comparable to that of zibotentan was observed by co-incubation with the ETAR antagonist (BQ123) (FIG. 7). Considering potency using a Schild Plot (pA2 analysis of the affinity of the antagonist for its receptor), zibotentan (n=8) has similar potency as BQ123 (n=6) as revealed by similar pA2 values (zibotentan 7.591 (95% CI 7.312 to 7.871) vs. BQ123 7.527 (95% CI 7.367 to 7.687)). BQ123 is not effective when given orally. The small rightward shift on the ET-1 CCRC with BQ788 (1 μMl, may reflects the low affinity of this compound for the ETA receptor (Russell & Davenport. Br J Pharmacol, 1996; 119(4):631). The BQ788 shift would be consistent with a pA2 of between 5.98-6.85 rather than a pA2 of 8 that would be expected if the constrictor response was mediated via the ETB receptor.

Conclusions: We have shown altered function of peripheral small arteries in patients with MVA compared with control subjects. Peripheral vascular abnormalities were characterised by endothelial impairment and increased responses to vasoconstrictor stimuli, notably ET-1. The enhanced response to ET-1 is mediated via the $ET_AR$ which may be upregulated or more active in patients with MVA. The ultra-selective ETAR antagonist (Zibotentan) is the most potent, orally active selective inhibitor of this detrimental ETAR mediated ET-1 vascular response in these patients. ETB antagonism with BQ788 had a negligible effect and, importantly, BQ123 is not orally active.

Summary: Our results suggest that ETAR are upregulated or more effective at mediating ET-1 vasoconstriction in patients with microvascular angina as compared to observations in matched control subjects.

Example 4: ET-1 SNP Genotype/Phenotype Interactions

A publication by Gupta et al (Cell, July 2017), identified rs9349379, a common non-coding SNP (PHACTR1 gene), as a downstream enhancer of ET-1 gene expression in human vascular cells.[25] A common genetic variant in chromosome 6p24 (rs9349379) associates with five vascular diseases (coronary artery disease, hypertension, fibromuscular dysplasia, migraine, and arterial dissection) in genome wide association studies it has been shown to be a distal regulator of endothelin gene expression. Specifically, the minor allele of the intronic single nucleotide polymorphism (SNP), rs9349379-G, is associated with increased risk of coronary artery disease, increased endothelin gene expression and ET-1 serum levels. ET-1 dysregulation was thus implicated in these vascular disorders, however the role of this SNP in the pathogenesis of CMD has not been examined. If there is a genetic basis for ET-1 mediated microvascular disease in the heart, then this finding would provide mechanistic support to advance the case for therapy development involving ETA modulation.

In light of the inventors' findings presented herein, the following research questions were asked:
1. Is there an association between genotype (rs9349379-G allele) and phenotype (MVA) in a prospective cohort of patients with stable chest pain?
2. Does the genotype associate with non-invasive parameters of myocardial ischemia and exercise capacity in microvascular angina subjects?
3. Vascular biology: what is the peripheral vascular ETA receptor response to ET-1 in subjects with genetically elevated ET-1 activity (SNP minor G allele)

Figure 8:
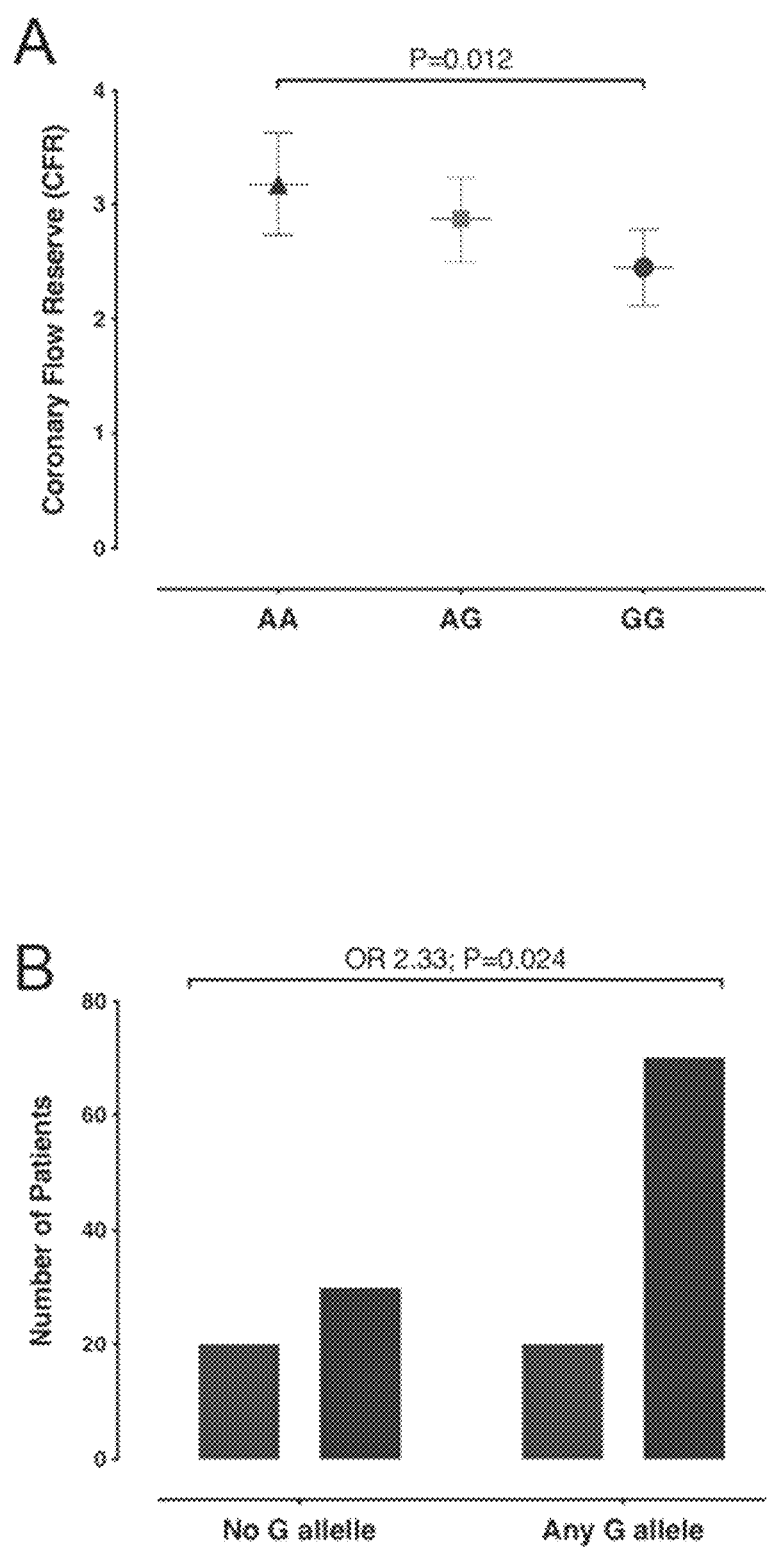
FIG. 8 A—Patients with genetically determined increased ET-1 gene expression (G allele) are over twice as likely to have microvascular angina (CMD) (Odds ratio 2.2; 95% CI 1.1-4.6). B—Coronary flow reserve (CFR—a marker of microvascular impairment in patients with INOCA) was lower amongst subjects with two high risk G alleles (rs9349379) consistent with detrimental effects of increased Endothelin gene expression on the coronary microcirculation (one-way ANOVA linear trend P=0.012). A priori analysis of AA v GG group showed lower CFR in the GG group consistent with worse CMD (mean difference 0.7, 95% CI 0.2-1.3; P=0.011).

A1—In patients with the genetic polymorphism (rs9349379-G allele) had more than a two-fold increase in the likelihood of CMD (OR 2.33; 95% CI 1.10-4.95; P=0.024; FIG. 8A). Multivariate analysis showed the G allele remained associated with CMD (OR per G allele 1.83; 1.03-3.27; P=0.04. Furthermore, coronary flow reserve (CFR—a measure of microvascular function) decreased linearly with each additional G allele (AA 3.2; AG 2.9; GG 2.4; P trend=0.012). The highest risk group (GG) had a significantly lower CFR than the AA group (mean difference 0.7, 95% CI 0.2-1.3; P=0.011; FIG. 8B).

Figure 9:
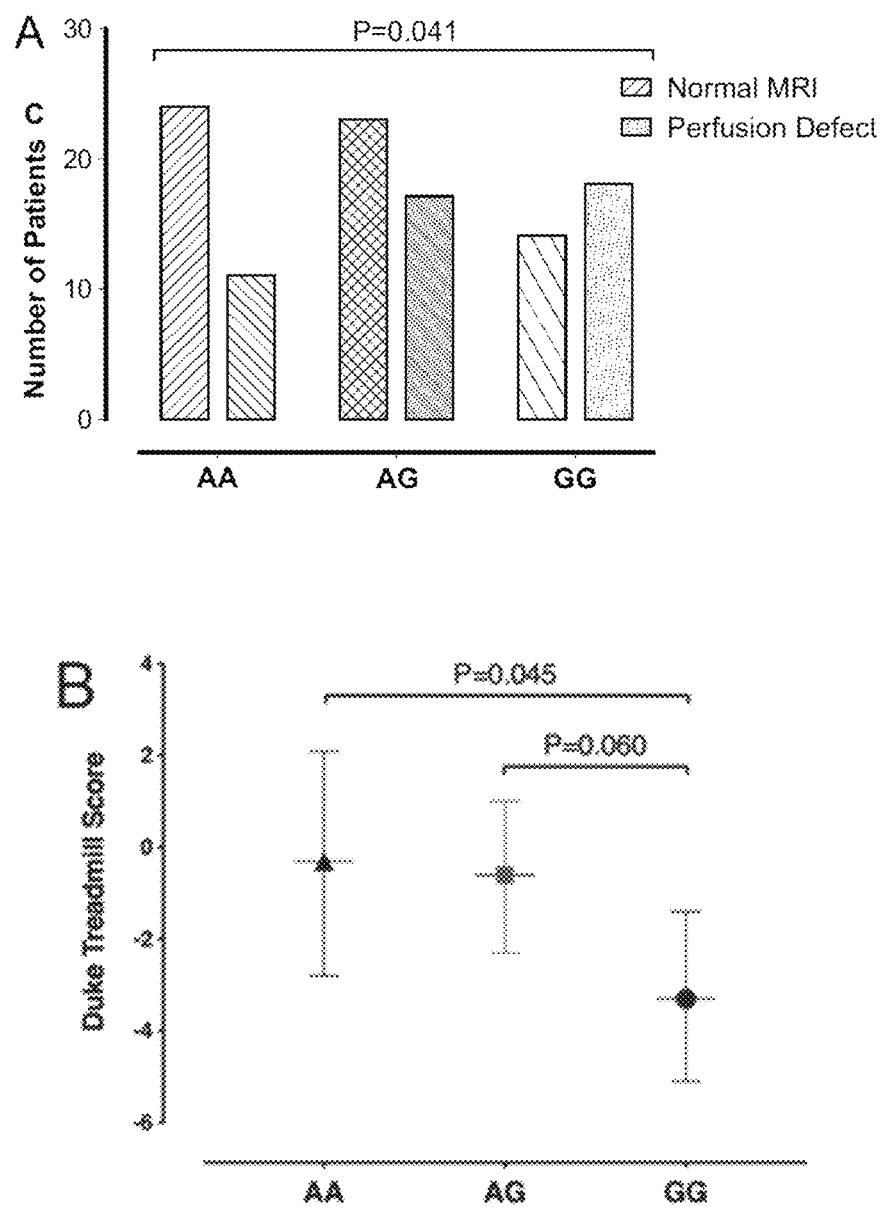
FIG. 9 Patients with genetically determined increased ET-1 gene expression (G allele) have worse ischaemia on non-invasive (Multimodality Assessment) A—Cardiac Stress Magnetic Resonance Imaging (N=107), There was a linear relationship between G allele and presence of an inducible perfusion defect on CMR ($\chi^2$ test for trend P=0.041). B—Exercise Treadmill Testing (n=84)—There was a negative linear relationship between genotype group and worsening ischemia on stress testing (Duke treadmill Score ANOVA P trend=0.045).
Figure 11:
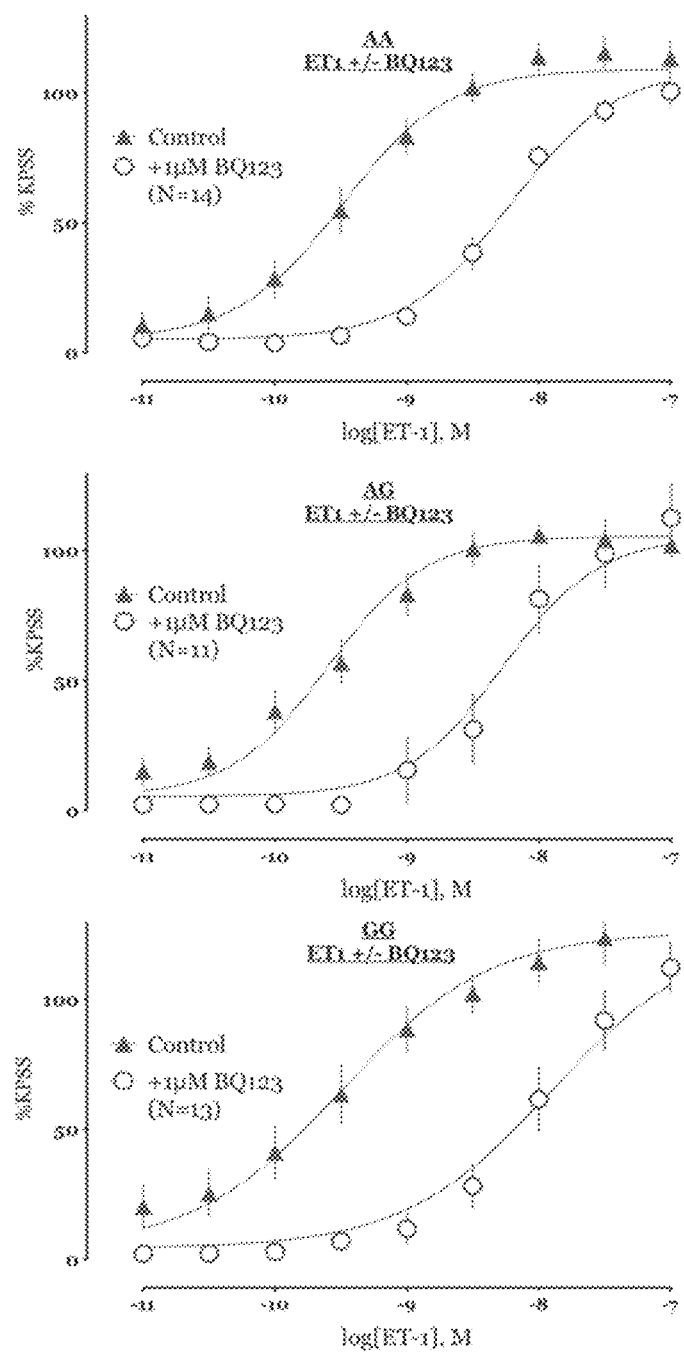
FIG. 11 Ex vivo pharmacological studies in the presence and absence of Endothelin A receptor modulation (ET$_A$R with BQ123). Three distinct groups of patients according to genetically determined ET-1 activity (AA genotype typically with the lowest Endothelin gene expression upto GG genotype typically with the highest Endothelin gene expression). Vasoconstriction was induced with ET-1 at the concentration shown on the x axis. We show similar antagonist potency (rightward curve shift) for each group suggesting firstly that the ET$_A$R are the dominant effectors of the ET-1 vasoconstrictor response. Secondly and more importantly, we show that the ET$_A$R pathway is not downregulated in spite of the elevated endothelin-1 gene expression and known increase in ET-1 activity in the G allele patients. This findings is particularly relevant when considering ET$_A$R pathway modulation with Zibotentan in subject with microvascular angina.

A2—The rs9349379-G allele was linearly associated with inducible ischemia on stress perfusion MRI (GG 56%, AG 43%, AA 31%; P=0.042, FIG. 99A). Ninety subjects completed exercise treadmill testing during a standard care diagnostic work up prior to invasive coronary angiography. The mean exercise duration was 367 (±156) seconds and similar between the groups. The mean Duke Treadmill Score (DTS) was −1.0 (±5.3) units. Considering the sub-group of 84 patients in whom genotype and DTS were both available, there was a lower DTS for each additional G allele (P=0.045). A priori analysis of subjects homozygous for the minor G allele compared to the AA group revealed a mean difference of −3.0 units (95% CI −5.8 to −0.1; P=0.045; FIG. 9B).

A3—We evaluated the underlying pathophysiology of ET-1 mediated vasoconstriction in human arterioles isolated from freshly explanted subcutaneous tissue according to genotype concluding that the $ET_A$ vasoconstrictor response is not downregulated in spite of the elevated endothelin gene expression and known increase in ET-1 activity in patients with the SNP. The selective $ET_A$ receptor antagonist peptide, BQ123, caused a parallel rightward shift of the CCRC to ET-1 in all arteries. $pK_B$ values derived using Schild regression were all similar between groups AA, AG and GG ($pK_B$ values of 7.07 [±0.23], 7.79 [±0.35] and 7.41 [±0.26] respectively; P=0.209) and were comparable to functional affinity values reported in the literature for this compound in other human blood vessels including epicardial coronary arteries.[26] Zibotentan also antagonized constrictor responses to ET-1 with $pK_B$ of 7.54 (N=8), comparable to that of BQ123 (FIG. 10A). More importantly these studies confirmed that Zibotentan produced a concentration-dependent inhibition of an established constrictor response to ET-1 (P<0.001; FIG. 10B).

From a population perspective, the Global and European minor allele frequency of rs9349379 are 38% and 40% respectively (1000 Genomes Project, http://www.internationalgenome.org/home), while our sample of selected patients with CMD shows an enrichment of the minor allele with G allele frequency of 46%.

Summary: This body of work supports the hypothesis that longstanding increased expression of the endothelin gene and resultant elevated tissue ET-1 activity is associated with pathological effects on the coronary microcirculation, leading in turn to impaired myocardial blood flow during stress testing as revealed by quantitative CMR, and impaired exercise capacity, in patients with microvascular angina. This hypothesis was consistently supported by results from the multi-modality studies employed in this investigation. Finally, the vascular biology substudies supports a role for the selective modulation of ETA receptor antagonist Zibotentan as a targeted agent in subjects with microvascular angina.

Example 5: Genetic Dysregulation of Endothelin-1 is Implicated in Coronary Microvascular Dysfunction Aims: Endothelin-1 (ET-1) is a potent vasoconstrictor peptide linked to vascular diseases through a common intronic gene enhancer [(rs9349379-G allele), chromosome 6 (PHACTR1/EDN1)]. We performed a multimodality investigation into the role of ET-1 and this gene variant in the pathogenesis of coronary microvascular dysfunction (CMD) in patients with symptoms and/or signs of ischaemia but no obstructive coronary artery disease (CAD).

Methods and results: Three hundred and ninety-one patients with angina were enrolled. Of these, 206 (53%) with obstructive CAD were excluded leaving 185 (47%) eligible. One hundred and nine (72%) of 151 subjects who underwent invasive testing had objective evidence of CMD (COVADIS criteria). rs9349379-G allele frequency was greater than in contemporary reference genome bank control subjects [allele frequency 46% (129/280 alleles) vs. 39% (5551/14380); P=0.013]. The G allele was associated with higher plasma serum ET-1 [least squares mean 1.59 pg/mL vs. 1.28 µg/30 mL; 95% confidence interval (CI) 0.10-0.53; P=0.005]. Patients with rs9349379-G allele had over double the odds of CMD [odds ratio (OR) 2.33, 95% CI 1.10-4.96; P=0.027]. Multimodality non-invasive testing confirmed the G allele was associated with linked impairments in myocardial perfusion on stress cardiac magnetic resonance imaging at 1.5 T (N=107; GG 56%, AG 43%, AA 31%, P=0.042) and exercise testing (N=87; −3.0 units in Duke Exercise Treadmill Score; −5.8 to −0.1; P=0.045). Endothelin-1 related vascular mechanisms were assessed ex vivo using wire myography with endothelin A receptor ($ET_A$) antagonists including zibotentan. Subjects with rs9349379-G allele had preserved peripheral small vessel reactivity to ET-1 with high affinity of $ET_A$ antagonists. Zibotentan reversed ET-1-induced vasoconstriction independently of G allele status.

Conclusion: We identify a novel genetic risk locus for CMD. These findings implicate ET-1 dysregulation and support the possibility of precision medicine using genetics to target oral $ET_A$ antagonist therapy in patients with microvascular angina.

Introduction

The coronary microcirculation has been implicated in the pathogenesis of angina for over 50 years, however, disease mechanisms remain incompletely understood.[1A] Coronary microvascular dysfunction (CMD) is associated with adverse outcomes in angina and a plethora of other cardiovascular disorders.[2A-5A] Standardized diagnostic criteria for microvascular dysfunction[6A] underpin recent studies which have identified the disease prevalence affecting twothirds of angina patients without obstructive epicardial coronary artery disease (CAD).[7A-10A] These patients present a diagnostic and therapeutic challenge with up to one in four experiencing a major adverse cardiac event after 5 years of follow-up.[11A,12A] The syndrome of ischaemia and no obstructive CAD (INOCA) is particularly important in women,[13A] whose elevated cardiac risk is mostly driven by impaired coronary flow reserve (CFR) (and not obstructive coronary disease).[11A]

Endothelin-1 (ET-1) is a highly potent endogenous vasoconstrictor of human coronary arteries[14A] and has been implicated in the pathogenesis of microvascular dysfunction.[15A,16A] Endothelin-1-mediated activation of the G protein-coupled endothelin A ($ET_A$) receptor on vascular smooth muscle cells induces endothelial dysfunction, inflammation, and vasoproliferative effects.

Circulating concentrations of serum ET-1 are inversely associated with coronary flow responses in patients with CMD.[14A,16A] Recently, a common (39%) genetic locus in chromosome 6p24 (PHACTR1/EDN1) has been shown to be a distal regulator of endothelin gene expression.[17A] The allele, rs9349379-G, is associated with an increased risk for atherosclerotic epicardial CAD and myocardial infarction.[18A] This functional single-nucleotide polymorphism (SNP: rs9349379-G) is associated with increased endothelin gene expression resulting in a lifetime's exposure at least 20% higher ET-1 precursor levels in the plasma.[17A] Endothelin-1 dysregulation is implicated in coronary vascular disease, however, the role of rs9349379 in the pathogenesis of CMD has not been examined. We investigated the association, if any, of the rs9349379-G allele with CMD in angina patients undergoing invasive coronary function testing. Our secondary objectives were to investigate whether the G allele associates with non-invasive parameters of myocardial ischaemia. Our final objective was to examine vascular mechanisms using isometric tension recordings in small peripheral resistance vessels isolated from patients according to genotype. We evaluated $ET_A$ receptor-mediated vasoconstriction in subjects according to rs9349379-G allele status. These included zibotentan, an $ET_A$ receptor-selective antagonist, which is available for repurposing following neutral results in phase 3 oncology trials.

Methods

Study population: We prospectively enrolled patients with stable angina. We screened elective adult referrals to two hospitals serving a population of ~2.5 million in the West of Scotland. Patients were scheduled to undergo clinically indicated invasive coronary angiography for the investigation of suspected CAD. The participants were enrolled into the Coronary Microvascular Angina (CorMicA) study (ClinicalTrials.gov: NCT03 193294), which was a randomized, controlled, strategy trial of stratified medicine in angina patients without obstructive CAD.[19A] Rose-Angina questionnaire was administered on the day of the angiogram and only patients with definite or possible angina were eligible to participate.[20A] Exclusion criteria included a non-coronary indication for invasive angiography, e.g. valve disease, severe renal dysfunction (glomerular filtration rate<30 mL/min), inability to give informed consent and obstructive coronary disease determined during invasive coronary angiography [≥50% diameter stenosis and/or fractional flow reserve (FFR)≤0.80]. All coronary vasodilating drugs were discontinued at least 24 h before the procedure. Pooled control genotype frequencies were ascertained from a contemporary medical genome reference cohort.[21A]

Definitions: Coronary Microvascular Dysfunction

We defined CMD using invasive coronary function testing and the Coronary Vasomotion Disorders International Study Group (COVADIS) diagnostic criteria.[20A] These physiological criteria included an abnormal response to adenosine [raised index of microvascular resistance (IMR) (≥25) and/or abnormal CFR (<2.0)]. In addition, CMD also included subjects with microvascular spasm during acetylcholine (ACh) provocation [reproduction of angina symptoms, ischaemic electrocardiogram changes 1 mm ST-segment deviation), but <90% epicardial spasm during ACh testing].[22A] Coronary microvascular dysfunction is frequently associated with epicardial vasospasm and hence patients with abnormal vasoreactivity during adenosine assessment (abnormal IMR and/or CFR) and coexistent epicardial vasospasm during ACh provocation were included within the CMD group.

Fractional flow reserve was measured to rule-out flow limiting CAD as an alternative explanation for myocardial ischaemia (INOCA subjects had an FFR>0.80 in target artery).

Measurement of Coronary Vascular Function In Vivo

We used an interventional diagnostic procedure (IDP) that combined guidewire-based direct measurement of coronary vascular function followed by pharmacological vasoreactivity testing. Specifically, the IDP included a guidewire-based measurement of coronary vascular function [FFR, CFR and IMR] followed by pharmacological vasoreactivity testing with ACh and glyceryl trinitrate (GTN) and has been previously described.[19A,23A]

In brief, an intravenous infusion of adenosine (140 µg kg$^{-1}$ min$^{-1}$) was administered via a large peripheral vein to induce steady-state maximal hyperaemia for a period of at least 90 s with a target time of 180 s. A pressure-temperature sensitive guidewire was placed into the distal third of a major epicardial coronary artery (typically the left anterior descending). The myocardial FFR was calculated by the ratio of mean distal coronary pressure to mean aortic pressure during maximal hyperaemia. A FFR 50.80 was taken as abnormal and indicative of flow-limiting CAD.[24A] Coronary flow reserve was calculated using thermodilution as resting mean transit time divided by hyperaemic mean transit time.[25A] A CFR<2.0 was defined as abnormal representing impaired vasodilator reserve.[26A] The IMR was calculated as the product of mean hyperaemic transit time and mean distal coronary pressure at hyperaemia.[27A] An IMR≥25 was defined as abnormal and indicative of increased microcirculatory resistance.[28A]

These invasive parameters were simultaneously derived in real time using dedicated software (Coroventis, Uppsala, Sweden). We assessed endothelium-dependent coronary vasomotor function using intracoronary infusions of ACh via the guiding catheter at concentrations of 0.182, 1.82, and 18.2 µg/mL (10$^{-6}$, 10$^{-5}$, and 10$^{-4}$ mol/L, respectively) at lmL/min for 2 min via a mechanical infusion pump.[29A] Patients who had CMD (e.g. abnormal CFR and/or IMR) but co-existent epicardial vasospasm during ACh bolus (100 µg bolus of ACh; 5.5 mL of 10$^{-4}$ mol/L over 20 s) were considered in the CMD group.[30A] In order to assess nonendothelial dependent vasodilatation, 300 µg of GTN was administered by manual intracoronary bolus injection. Detailed methods are reported in the Supplementary material online, Appendix.

Blood and Tissue Analysis

Serum ET-1 was determined using blood obtained on the day of coronary function testing (Quantikine® ELISA, R&D Systems® Europe, Abington, UK). Blood was obtained from participants following an overnight fast in a recumbent position.

Ex vivo pharmacological assessment of peripheral vascular function was performed on patients who volunteered to undergo a gluteal skin fat biopsy within 4 weeks of the invasive coronary function assessment. The biopsy was obtained under sterile conditions using local anaesthesia with lidocaine (2%). Small peripheral resistance vessels (<400 µm) were carefully dissected from fresh biopsies using a light microscope. About 2 mm length vessels were mounted on 40-µm stainless steel wires for isometric myography in multi-channel myograph chambers (DMT, Denmark) filled with physiological saline solution. Isometric tension recordings followed on directly using the technique of wire myography to study small peripheral resistance arteries with paired cumulative concentration response curves (CCRCs) to ET-1 in the presence or absence of an ET$_A$ receptor antagonist, either BQ123 or zibotentan (AstraZeneca, UK; Open Innovation). This vascular biology substudy was an extension of our work in INOCA subjects that was previously published in this journal.[31A] The detailed methods are described in the Supplementary material online, Appendix.

The peripheral vascular sensitivity to ET-1 (pEC$_{50}$) and maximum vasoconstriction to ET-1 (Eu$_{max}$) were determined. For the antagonist studies, the affinity (K$_B$) of BQ123 was first determined in paired vessels from individuals and calculated using Schild regression. The pK$_B$ (−log$_{10}$ K$_B$) values were compared between each genotype as an indicator of whether or not patients of different genotypes are likely to respond equally well to an ET$_A$ antagonist used clinically. A final series of experiments involved paired vessel experiments using ET-1 CCRCs in the presence and absence of a highly selective ET$_A$ receptor antagonist, zibotentan to determine a pKB value and assess whether zibotentan could reverse an established ET-1-mediated vessel constriction.

Cardiac Magnetic Resonance Imaging and Ischaemia Testing Protocol

Patients were prospectively invited to undergo quantitative perfusion cardiac magnetic resonance (CMR) imaging at 1.5 T using pharmacological stress testing with intravenous adenosine (140 µg/kg/min) within 6 weeks of the index coronary angiogram. CMR studies were performed using a standardized CMR protocol (Siemens MAGNETOM Avanto, Erlangen, Germany). The CMR scans were interpreted by two experienced observers (D.C., C.B.) with Level III accreditation of the European Association of Cardiovascular Imaging (EACVI), blind to diagnostic findings and genotype. The raw stress and rest perfusion images were qualitatively assessed for inducible or fixed perfusion defects. The perfusion was classified as either normal, abnormal, or equivocal. If a perfusion defect was present, it was reported as having an epicardial, microvascular or equivocal pattern. Perfusion defects were then reported on a segmental basis according to the American Heart Association 16-segment model[32A] and were classified according to the transmurality of the perfusion defect (<50% or >50%), and the number of segments with qualitatively abnormal perfusion was defined. Dark rim artefact was adjudicated based on standardized criteria.[33A]

The first-pass perfusion images were then post-processed to derive quantitative pixel perfusion maps to derive absolute myocardial blood flow and myocardial perfusion reserve (MPR) (further detail in Supplementary material online).[34A]

Treadmill exercise stress electrocardiography using the Bruce protocol was analysed from the subgroup of patients who had been pre-selected for this procedure on clinical grounds prior to invasive coronary angiography. We used the Duke treadmill score (DTS) which is a validated metric with established prognostic cardiovascular utility.[35A] The exercise treadmill test analysis included (i) exercise duration and (ii) the DTS[36A] by a cardiology researcher (EY) blinded to genotype and invasive physiology. The DTS is based on the occurrence of angina during treadmill exercise testing, ST-segment depression during the test and peak exercise duration (or metabolic equivalent of task achieved). Specifically, the DTS equals the maximum exercise time in minutes−(5 the maximal net ST-segment deviation in mm during or after exercise)–(4 the treadmill angina index (where 0=no angina, 1=non-limiting angina, 2=exercise limiting angina).

All subjects were asked to abstain from caffeine-containing beverages or foodstuffs for 24 h, and vasoactive medications for 48 h prior to the CMR examination. All scan acquisitions were spatially co-registered. All CMR analyses were performed by a blinded analyst with Level 3 EACVI 110 accreditation.

Statistical Analysis

The main hypothesis in our study was that regulation of ET-1 gene expression reflected by the presence of the intronic ET-1 gene enhancer, rs9349379-G, associates with invasive tests of CMD. We tested the association of genotype (SNP rs9349379 G-A allele status) with CMD on invasive coronary vasoreactivity testing by calculating the odds ratio (OR) and its 95% confidence intervals (CIs). Multivariable logistic regression was used to determine whether genotype was independently associated with CMD (as defined by abnormal response to intracoronary ACh and/or systemic adenosine) adjusting for overall cardiac risk (ASSIGN score) including previous cardiac events.[37,4]

Categorical data are presented as percentages and continuous parameters are shown as means with standard deviation values or medians with interquartile ranges. For secondary analyses, subjects were divided into three genotype groups. Kruskal-Wallis test was used to test whether distribution of non-parametric variables is the same between the groups. Subgroup analysis of A vs. G genotypes was determined a priori to evaluate any differences between the two most differentiated groups. The least squares (LS) mean of serum ET-1 levels was compared between the groups derived using analysis of co-variance with serum ET-1 as dependent variable and adjusted for age, sex, bodymass index, genotype and cardiovascular risk as covariates and possible confounders. Linear associations with invasive and non-invasive metrics of microvascular disease were performed by analysis of variance (ANOVA) with P for linear trend for continuous parameters and ×2 test with P for linear-by-linear test for categorical variables. Statistical analyses were performed with Prism 7.0 (GraphPad, La Jolla, CA, USA) and SPSS 25.0 (SPSS, Chicago, IL, 20 USA).

Results

Figure 12:
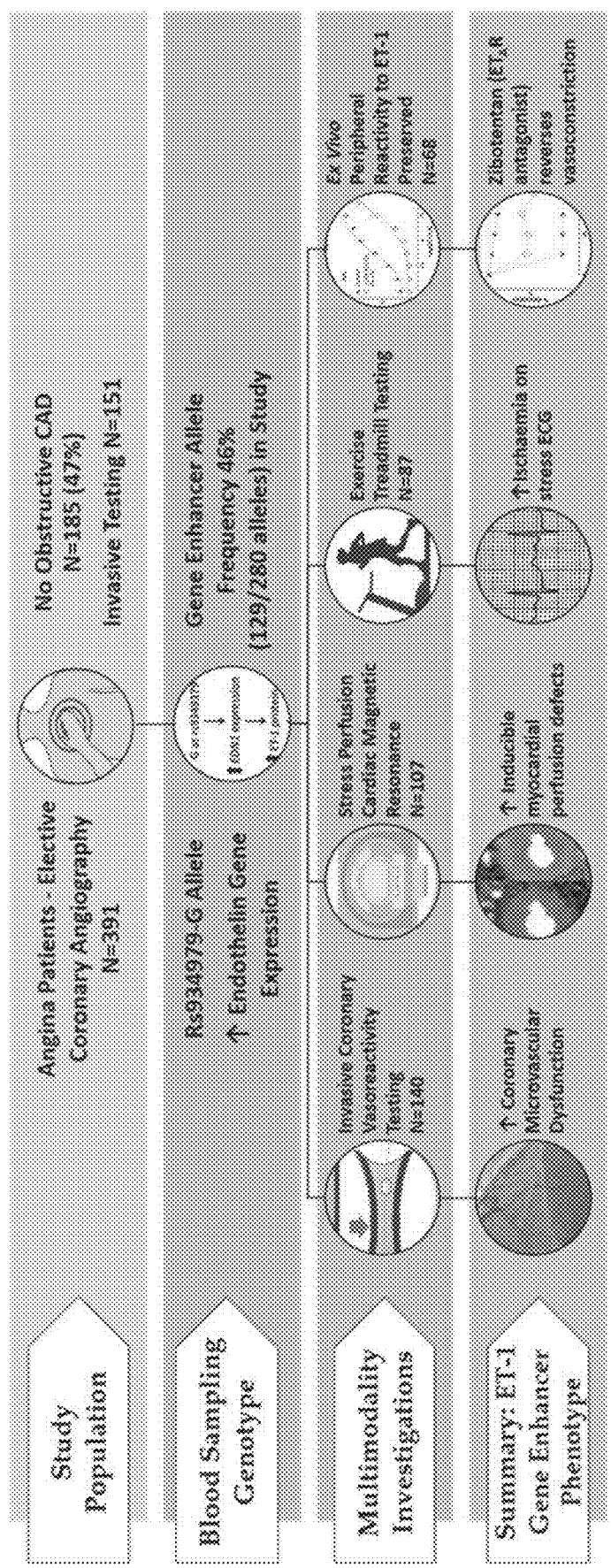
FIG. 12 Study overview: endothelin-1 gene enhancer in microvascular angina. Three hundred and ninety-one patients with stable angina were prospectively enrolled without prior knowledge of coronary anatomy. One hundred and eighty-five (47%) had no obstructive coronary artery disease and thus eligible for invasive coronary vasoreactivity testing and further sub-studies. One hundred and fifty-one of 185 (82%) were able to undergo adjunctive invasive tests for coronary microvascular dysfunction. One hundred and nine (72%) subjects tested had evidence of coronary microvascular dysfunction. One hundred and forty subjects underwent genetic analysis for rs9349379-G allele with an allele frequency of 46% (129/280 alleles). The frequency of detrimental G alleles was higher than reference genome bank control subjects (46% vs. 39%; P=0.013). Patients with rs9349379-G allele had higher serum endothelin-1 and over double the odds of coronary microvascular dysfunction (odds ratio 2.33, 95% confidence interval 1.10-4.96; P=0.027). In addition, subjects were more likely to have impaired myocardial perfusion (P=0.04) and exercise tolerance (−3.0 units in Duke Exercise Treadmill Score; P=0.045). Peripheral small artery reactivity to endothelin-1 and affinity of ET$_A$ receptor antagonists were preserved in the rs9349379-G allele group (P=0.209). Crucially, zibotentan tested at clinically relevant concentrations, fully reversed an established endothelin-1 vasoconstriction, indicative of efficacy in conditions associated with vasospasm. This suggests that ET$_A$ receptor antagonism in this group of patients may have therapeutic benefit.

We prospectively enrolled 391 patients with angina between 25 Nov. 2016 and 11 Dec. 2017 at two hospitals serving a population of ~2.5 million in the West of Scotland (CorMicA: ClinicalTrials.gov NCT03193294).[19,4] Invasive coronary angiography revealed obstructive disease in 206 (53.7%) participants who were then excluded from further study. One hundred and fifty-one participants with no obstructive coronary disease continued in the study (FIG. 12. Table 2). Evidence of CMD was found in 109 (72%) of 151 subjects undergoing invasive coronary vasoreactivity testing (Table 3). An overview of the study and investigations is illustrated in FIG. 12. Genetic analysis was completed in 140 subjects (93%) using baseline venous blood samples. The mean age of patients in this analysis 61.1±10.1 years. There was a predominance of women [103 (74%)] and the estimated 10-year risk of cardiovascular events (ASSIGN) was appreciable at 25% (±20).

Figure 13:
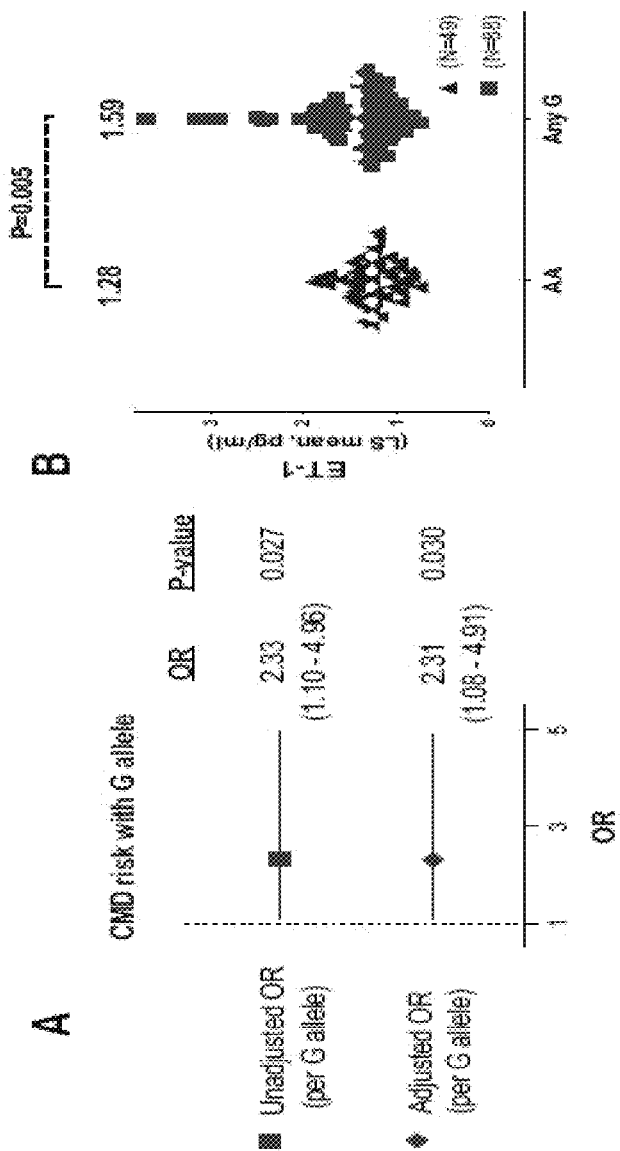
FIG. 13 Detrimental effects of rs9349379-G allele on coronary microvascular function and endothelin-1. (A) Patients with G allele were over twice as likely to have underlying microvascular dysfunction (odds ratio per G allele 2.33, 95% confidence interval 1.10-4.96; P=0.027) Even after adjustment for other risk factors the G allele was predictive of microvascular disease (odds ratio 2.31; 95% confidence interval 1.0-4.91). This finding supports a detrimental impact on the coronary microcirculation of a lifetime of increased endothelin gene expression. (8) In a multivariable regression model adjusting for baseline group differences, patients with rs9349379-G allele had higher plasma endothelin-1 (least squares mean 1.59 pg/mL vs. 1.28 pg/mL; 95% confidence interval 0.10-0.53; P=0.005).

The genotype distribution of rs9349379 was AA (N=50, 36%), AG (N=51, 36%), and GG (N=39, 28%). This SNP did not fulfil Hardy Weinberg equilibrium (P=0.0015) reflecting biologic ascertainment of genotypes. One hundred and forty subjects underwent genetic analysis for (rs9349379-G allele) with an allele frequency of 46% (129/280 alleles). The allele frequency was increased in our angina cohort compared to that of genome bank control subjects [rs9349379-G allele frequency 39% (5551/14380); $x^2$=6.15, P=0.013].[21,4] The rs9349379-G allele was associated with over double the odds of CMD (OR 2.33, 95% CI 1.10-4.96; P=0.027; FIG. 13A). Subjects with G allele had higher circulating serum ET-1 concentration (LS mean 1.59 pg/mL vs. 1.28 pg/mL; difference 0.31 pg/mL; 0.10-0.52; P=0.005; FIG. 13B). Each additional G allele was linearly associated with CMD on invasive interrogation (FIG. 14A; P=0.021). On multivariable analysis, the G allele remained associated with CMD (OR per G allele 2.31; 1.08-4.91; P=0.030).

TABLE 2

Baseline demographics by genotype

| | SNP (rs9349379) genotype (n = 140) | | | |
|---|---|---|---|---|
| | AA (N = 50) | AG (N = 51) | GG (N = 39) | P-value[a] |
| Clinical features | | | | |
| Age (years) | 60.6 (±11) | 61.1 (±10) | 61.6 (±10) | 0.649 |
| Female | 36 (72%) | 36 (71%) | 31 (80%) | 0.607 |
| ASSIGN score[b] | 24 (±21) | 27 (±23) | 25 (±19) | 0.811 |
| Dyslipidaernia | 12 (24%) | 10 (20%) | 8 (21%) | 0.671 |
| Hypertension | 30 (60%) | 32 (63%) | 27 (69%) | 0.382 |
| Previous cardiovascular event[c] | 10 (20%) | 10 (20%) | 13 (33%) | 0.239 |
| Diabetic | 9 (18%) | 11 (22%) | 6 (15%) | 0.794 |
| Smoker | 6 (12%) | 8 (16%) | 9 (23%) | 0.169 |
| Family history | 17 (34%) | 13 (26%) | 13 (33%) | 0.886 |
| Peripheral vascular disease | 2 (4%) | 3 (6%) | 2 (5%) | 0.789 |
| Atrial fibrilation | 5 (10%) | 4 (8%) | 1 (3%) | 0.195 |
| Pulse (rate/min) | 69 (±11) | 67 (±11) | 71 (±11) | 0.697 |
| Systolic blood pressure (mmHg) | 138 (±22) | 136 (±31) | 138 (±25) | 0.951 |
| Diastolic blood pressure (mmHg) | 73 (±11) | 74 (±15) | 70 (±12) | 0.260 |
| Body mass index (kg/m$^2$) | 30.4 (±8) | 30.4 (±6) | 29.4 (±7) | 0.515 |
| Laboratory investigations | | | | |
| Cholesterol (mmol/L) | 3.5 (±1) | 3.5 (±1) | 3.6 (±1) | 0.904 |
| Glucose (mmol/L) | 4.6 (±1) | 5.0 (±2) | 4.7 (±2) | 0.774 |

TABLE 2-continued

Baseline demographics by genotype

| | SNP (rs9349379) genotype (n = 140) | | | |
|---|---|---|---|---|
| | AA (N = 50) | AG (N = 51) | GG (N = 39) | P-value[a] |
| C-reactive protein (mg/L) | 3.2 (±5) | 3.2 (±5) | 3.1 (±4) | 0.920 |
| N-terminal brain natriuretic peptide (pg/mL) | 140 (±187) | 157 (±197) | 135 (±153) | 0.937 |
| Endothelin-1 (pg/mL)[d] | 1.27 (0.42) | 1.41 (0.63) | 1.46 (0.56) | 0.097 |

Data are expressed as mean (standard deviation) or number (%).
ACE-I, angiotensin converting enzyme inhibitor;
ACh, acetylcholine;
BMI, body mass index;
CCB, calcium channel blocker;
CFR, coronary flow reserve;
FFR, fractional flow re- serve;
IMR, index of microcirculatory resistance;
LVEDP, left ventricular end-diastolic pressure;
MI, myocardial infarction.
[a]P-value represents between group ANOVA for linear trend (continuous data) or Pearson $v^2$ test for linear trend (categorical data) or Kruskal-Wallis testing probability that the distribution of non-parametric variables are the same across the groups.
[b]ASSIGN risk-predicted 10-year risk of cardiovascular event.
[c]Previous myocardial infarction or cerebrovascular event (including transient ischaemic attack).
[d]Endothelin-i levels were available in 137 genotyped subjects with significance determined using one-way ANOVA (linear trend).

Figure 14:
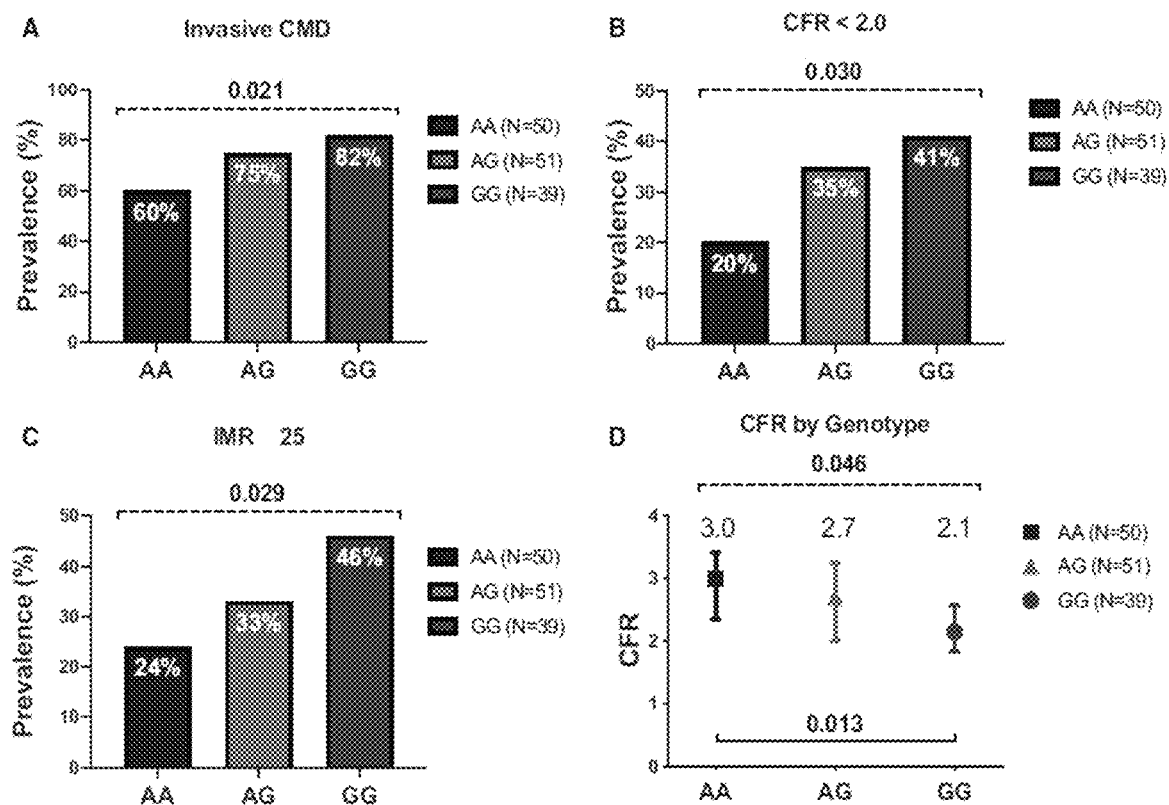
FIG. 14 Genotype: phenotype association of G allele with invasive coronary microvascular dysfunction. (A-C) The prevalence of microvascular dysfunction detected during invasive coronary testing was associated with genotype status (AA 60%, AG 75%, GG 83%; P=0.021). Presence of abnormal coronary flow reserve and microcirculatory resistance were linearly associated with each additional G allele. P-value represents Pearson v2 test for linear trend (categorical data). (D) Coronary flow reserve was lower amongst subjects with two high-risk G alleles (rs9349379) consistent with detrimental effects of increased endothelin gene expression on the coronary microcirculation (Kruskal-Wallis between groups dotted line, P=0.046). A priori subgroup analysis (AA vs. GG group—solid line) showed lower CFR in the GG group (P=0.013). Data are median CFR plus error bars represent 95% confidence intervals for the median. P=0.021, P=0.030, P=0.029 and P=0.056.

Considering diagnostic subtypes of microvascular dysfunction, the vast majority had CMD during adenosine interrogation (73% abnormal CFR and/or IMR) and only 27% of the genotyped population had isolated microvascular spasm (isolated CMD to ACh only). There was a statistically significant relationship between genotype and CMD, as reflected by an impaired coronary vasodilator reserve (abnormal CFR: AA 20%, AG 35%, and GG 41%; FIG. 14B; P=0.030). A similar relationship was noted for prevalence of abnormal microvascular resistance in each genotype (abnormal IMR: AA 24%, AG 33%, and GG 46%; FIG. 14C; P=0.029). Coronary flow reserve decreased linearly with each additional rs9349379-G allele [AA 3.0 (2.1-3.7); AG 2.7 (1.8-3.5); GG 2.1 (1.7-3.2); overall P=0.046; FIG. 14D; Table 3]. The highest risk group (GG) had a significantly lower CFR than the AA group (median difference 0.84, 95% CI 0.1111.1). The prevalence of abnormal invasive ACh response was not statistically different between the groups (any G allele 36% vs. no G allele 30%, P=0.463). Patients with isolated CMD to ACh (microvascular spasm) had similar ET-1 levels to those without (1.33 ng/mL vs. 1.28 ng/mL; P=0.769). The highest serum ET-1 levels were seen in subjects with concordant abnormalities in both CFR and IMR with linear stepwise reduction compared to those with only one index of CMD and lowest in those without any abnormalities [mean 1.67 ng/mL (both) vs. 1.39 ng/mL (one) vs. 1.31 ng/mL (none); P trend=0.041].

TABLE 3

Invasive coronary physiology and non-invasive stress testing

| | SNP (rs9349379) genotype | | | |
|---|---|---|---|---|
| | AA (N550) | AG (N551) | GG (N539) | P-value[a] |
| Minor non-obstructive CADb | 25 (50%) | 30 (59%) | 24 (62%) | 0.265 |
| Coronary atheroma burden (Gensini score)c | 0 (0.2) | 2 (0.5) | 1 (0.6) | 0.037 |
| Left ventricular end-diastolic pressure (mmHg) | 10 (±4) | 10 (±5) | 9 (±3) | 0.520 |
| Fractional flow reserve (FFR) | 0.88 (0.05) | 0.88 (0.06) | 0.88 (0.05) | 0.977 |
| Coronary microvascular dysfunction (any) | 30 (60%) | 38 (75%) | 32 (82%) | 0.021 |
| Abnormsal CFR (<2.0) | 10 (2.0%) | 18 (36%) | 16 (41%) | 0.030 |
| Coronary flow reserve (CFR) | 3.0 (21-3.7) | 2.7 (1.8-3 5) | 2.1 (1.7-3.2) | 0.046 |
| Abnormal IMR (>25) | 12 (24%) | 17 (33%) | 18 (46%) | 0.029 |
| Microcirculatoryresistance (IMR) | 18.9 (15.2-24.2) | 18.6 (14.2-29.3) | 22.1 (13.8-29.3) | 0.879 |
| Abnormal CFR or IMR | 20 (40%) | 26 (51%) | 27 (69%) | 0.007 |
| Microvascular spasm (during acetylcholine) | 15 (30%) | 21 (42%) | 12 (31%) | 0.385 |
| Exercise treadmill testing (N = 87) | 28 (56%) | 34 (67%) | 25 (64%) | |
| Duration (s) | 393 (±124) | 352 (±157) | 384 (±162) | 0.827 |
| METs | 7.8 (+2.1) | 7.4 (±2.6) | 7.6 (+2.1) | 0.786 |
| Angina on treadmill | 16 (59%) | 23 (68%) | 20 (87%) | 0.036 |
| Peak systolic blood pressure (mmHg) | 178 (±30) | 173 (±34) | 182 (±25) | 0.688 |
| Duke Treadmill Score | −0.3 (±6.0) | ±0.6 (±4.7) | ±3.3 (±4.2) | 0.045 |
| Stress perfusion magnetic resonance imaging (N =107) | | | | |
| Inducible myocardial perfusion defect | 11 (31%) | 17 (43%) | 18 (56%) | 0.042 |
| Inducible myocardial perfusion defect with CMD | 4 (13%) | 14 (37%) | 15 (47%) | 0.016 |
| Myocardial perfusion reserve (global) | 1.8 (±0.4) | 1.7 (±0.4) | 1.6 (±0.4) | 0.154 |
| Myocardial perfusion reserve (endocardium) | 1.7 (±0.4) | 1.6 (±0.4) | 1.5 (±.4) | 0.162 |
| Left ventricular end diastolic volume (indexed, mL/m²) | 68.5 (±13.6) | 70.1 (±13.2) | 70.2 (±11.9) | 0.591 |
| Left ventricular end systolic volume (indexed, mL/m²) | 23.4 (±6.0) | 25.4 (±8.8) | 23.1 (±5.8) | 0.848 |

TABLE 3-continued

Invasive coronary physiology and non-invasive stress testing

| | SNP (rs9349379) genotype | | | |
|---|---|---|---|---|
| | AA (N550) | AG (N551) | GG (N539) | P-value[a] |
| Left ventricular ejection fraction (%) | 65.9 (±4.4) | 64.5 (±6.5) | 67.3 (15.2) | 0.321 |
| Stroke volume (indexed, mL/m$^2$) | 45.0 (±8.8) | 44.7 (±7.0) | 47.1 (±8.2) | 0.298 |
| Left ventricular mass (indexed, mL/m$^2$) | 42.0 (±7.0) | 42.3 (±8.1) | 42.1 (±7.8) | 0.924 |

Data are expressed as mean (±SD), median (IQR), or N (%).
CAD, coronary artery disease;
CFR, coronary flow reserve;
FFR, fractional flow reserve;
LVEDP, left ventricular end-diastolic pressure;
IMR, index of microcirculatory resistance;
METS, metabolic equivalent of task.
[a]P-value represents between group ANOVA for linear trend (continuous data) or Pearson v2 test for linear trend (categorical data), Kruskal-Wallis test of probability that the distribution of non-parametric variables are the same across the groups.
[b]Core-laboratory adjudication of any angiographic evidence of coronary atherosclerosis including any minimal angiographic luminal irregularity.
[c]Gensini angiographic score is a metric of angiographic disease severity incorporating lesion severity and location. Detailed MRI methodology available in Supplementary material online, Appendix.

The Gensini angiographic score reflecting the extent (or burden) of coronary atherosclerosis was higher in the rs9349379-GG group [median score 1.0 (0.0-6.0)] compared to the AA group [median score 0.0 (0.0-2.0); P=0.037; Table 3]. As might be expected in this population of INOCA patients, the physiological burden of epicardial CAD was similar between the groups [myocardial FFR, AA 0.88 (±0.05); AG 0.88 (0.06); GG 0.88 (±0.05); P=0.977].

Figure 15:
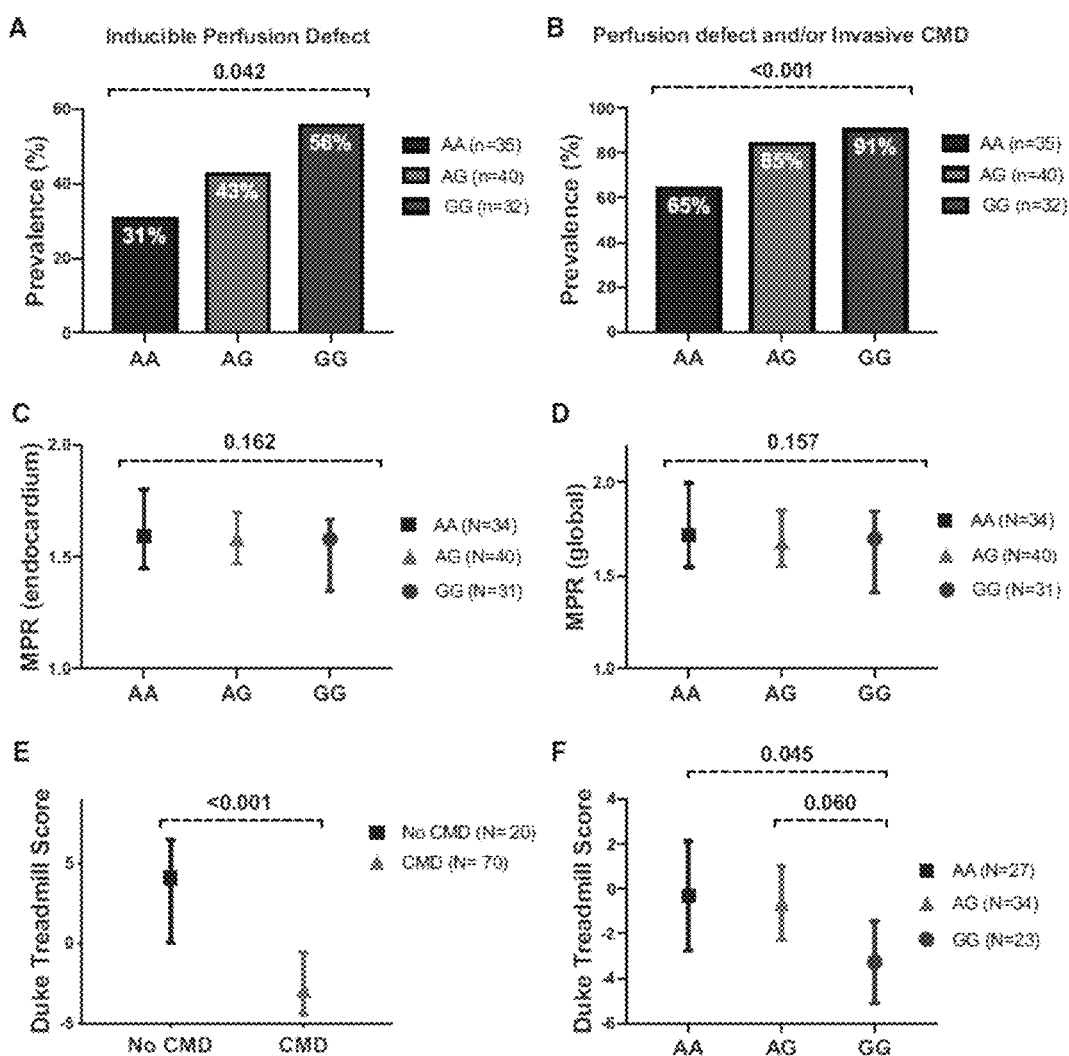
FIG. 15 Genotype: phenotype association of G allele with invasive coronary microvascular dysfunction. (A-C) The prevalence of microvascular dysfunction detected during invasive coronary testing was associated with genotype status (AA 60%, AG 75%, GG 83%; P=0.021). Presence of abnormal coronary flow reserve and microcirculatory resistance were linearly associated with each additional G allele. P-value represents Pearson $v^2$ test for linear trend (categorical data). (D) Coronary flow reserve was lower amongst subjects with two high-risk G alleles (rs9349379) consistent with detrimental effects of increased endothelin gene expression on the coronary microcirculation (Kruskal-Wallis between groups dotted line, P=0.046). A priori subgroup analysis (AA vs. GG group—solid line) showed lower CFR in the GG group (P=0.013). Data are median CFR plus error bars represent 95% confidence intervals for the median. P=0.021, P=0.030, P=0.029 and P=0.056.

One hundred and seven subjects underwent an adenosine stress perfusion cardiac magnetic resonance imaging (MRI) within 6 weeks of the invasive angiogram. Forty-six (43%) patients had evidence of a sub-endocardial circumferential abnormality of myocardial perfusion attributable to CMD (Table 3). The rs9349379-G allele was associated with abnormal myocardial perfusion disclosed by stress perfusion MRI (AA 31%, AG 43%, GG 56%; P=0.042, FIG. 15A). The association of genotype with CMD was more robust when considering subjects with either a circumferential subendocardial perfusion defect disclosed by MRI or invasive evidence of CMD (AA 65%, AG 85%, GG 91%; P<0.001; FIG. 15B). The absolute global and subendocardial perfusion reserve (MPR) was numerically lower with each G allele; however, the differences were not statistically significant (Table 3; FIGS. 15C and D).

We then assessed relationships between exercise treadmill testing, invasive measures of coronary vascular function and genotype. Ninety subjects prospectively completed exercise treadmill testing during standard care diagnostic work up prior to invasive coronary angiography, 84 of these subjects were included in the study with the remainder being excluded due to lack of genotype data. The mean exercise duration was 367 s (±156 s) and similar between the groups (Table 3). The mean DTS was −1.0 (±5.3) units. The presence of CMD was associated with reduced DTS (CMD −2.3 vs. no CMD +3.5; difference −5.8 units, 95% CI −8.2 to −3.3; P<0.001; FIG. 15E).

Overall, there was a moderate inverse correlation between presence of CMD and the DTS (Spearman's rho=−0.42; P<0.001). Considering the cohort of 84 patients in whom genotype and DTS were both available, there was a lower DTS for each additional G allele consistent with increasing ischaemia with ET-1 gene enhancement. A priori analysis of high-risk subjects (homozygous for the minor G allele) compared to the AA group revealed a mean difference of −3.0 units in DTS (95% CI −5.8 to −0.1; P=0.045) (FIG. 15F).

There was a modest correlation between the continuous DTS and genotype (Spearman's rho −0.21; P=0.055), that was not statistically significant. The angina index during exercise was linearly associated with G allele status (non-limiting or limiting angina AA 59% vs. AG 68% vs. GG 87%; P trend=0.036). The exercise time was not significantly lower amongst subjects with the G allele (365 vs. 392 s; P=0.423).

Sixty-eight genotyped subjects agreed to participate in a vascular biology sub-study, providing written informed consent for a gluteal subcutaneous biopsy within 4 weeks of coronary angiography. Subjects who volunteered to have a biopsy were of similar age and cardiac risk to those who declined to participate in the sub-study [biopsy participants mean age 62±9 years vs. 61±11 years (P=0.134), ASSIGN score 23%±18 vs. 28%±23 (P=0.198)]. Forty-four (65%) of these patients had biopsies with a sufficient number of small arteries to undergo paired CCRCs to ET-1 in the presence and absence of an $ET_A$ receptor antagonist, either BQ123 or zibotentan (ZD4054; AstraZeneca, Cambridge, UK).

Figure 16:
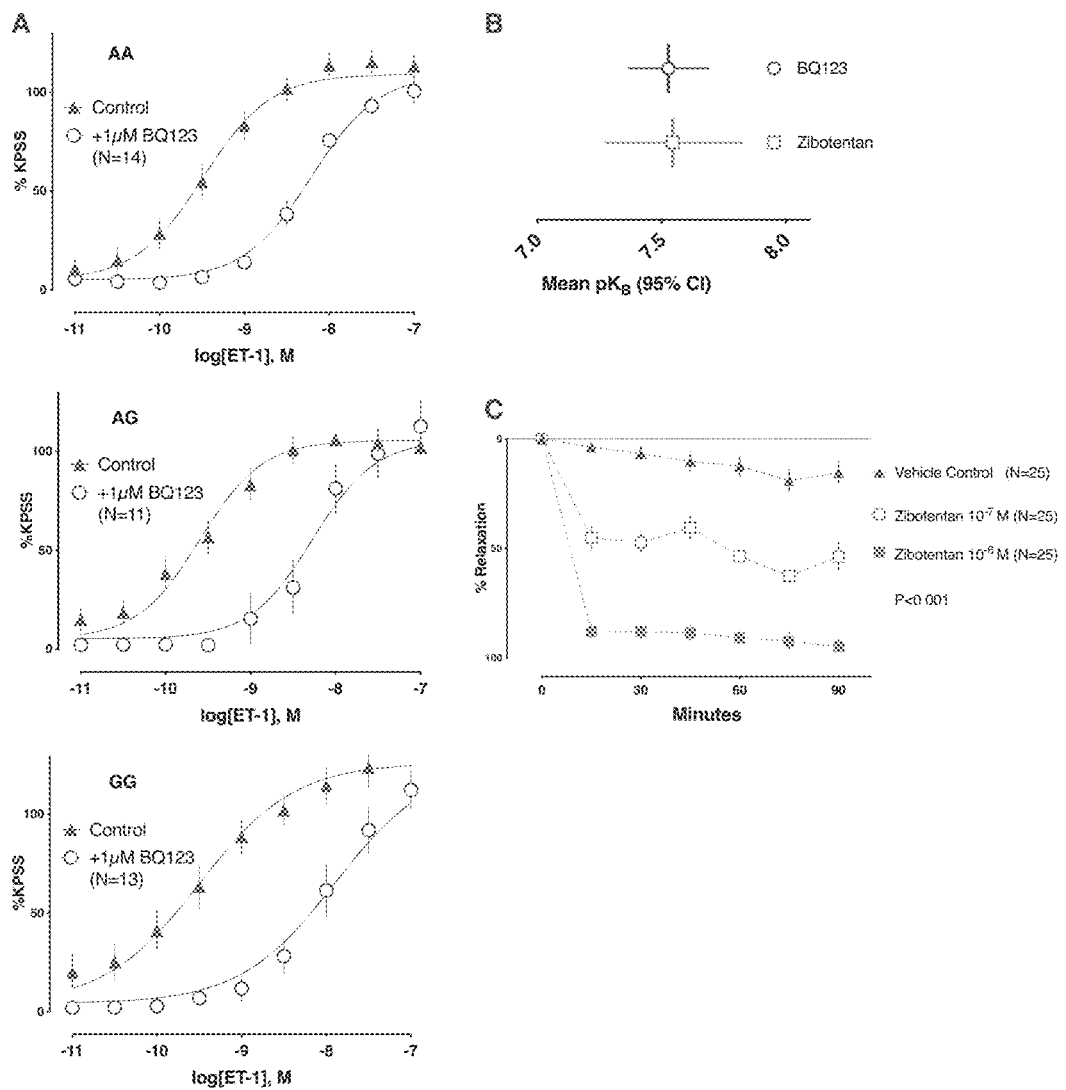
FIG. 16 Endothelin-1 ex vivo vascular biology by genotype. (A) Cumulative concentration response curve to endothelin-1 in the three groups in the presence and absence of ET$_A$ antagonist BQ123 (n=44). Similar antagonist potency (rightward curve shift) for each group suggesting firstly that the ET$_A$ receptors are the dominant effectors of the endothelin-1 vasoconstrictor response and secondly that the ET$_A$ receptor pathway is not down-regulated in spite of the elevated endothelin-1 gene expression and known increase in endothelin-1 activity in the G allele single-nucleotide polymorphism patients. (B) Antagonist potency of novel therapeutic oral $ET_A$ receptor antagonist zibotentan [N=8, mean 7.54 (95% confidence interval 7.27-7.82)] is similar to peptide antagonist BQ123 [N=27, mean 7.53 (95% confidence interval 7.37-7.69)]. Higher $pK_B$ represents a higher antagonist potency. (C) Zibotentan: reversal of established endothelin-1 vasoconstriction. Proof of concept dose-dependent reversal of potent and established endothelin-1-mediated peripheral arteriolar vasoconstriction. Crucially, the highest concentration tested which is also the plasma concentration achieved by a clinically relevant dose of 10 mg/day rapidly and fully reversed the established endothelin-1 constrictor response, indicative of efficacy in conditions of vasospasm. Comparison using ordinary two-way analysis of variance including time and dose both significant factors ($P<0.001$ after adjustment for multiple testing).

Grouping according to genotype (AA, n=16; AG, n=14; GG, n=14) and vasodilator responses to ACh (ACh $E_{max}$) were similar (Table 4). Similarly, vessels had similar potency for ET-1 ($pEC_{50}$ AA 9.34, AG 9.45, and GG 9.32; P=0.533) and maximum vasoconstriction to ET-1 ($E_{max}$ AA 122.3%, AG 115.5%, GG 129.7%; P=0.533; FIG. 16A; Table 4). Notably, the selective ETA receptor antagonist, BQ123, caused a parallel rightward shift of the CCRC with comparable $pK_B$ values between groups AA, AG, and GG [$pK_B$ values of 7.07 (±0.23), 7.79 (±0.35), and 7.41 (±0.26), respectively; P=0.209; FIG. 16B]. Zibotentan, a highly selective orally active ETA receptor antagonist, attenuated the constrictor response to ET-1 with $pK_B$ of 7.54 (95% CI 7.27-7.82), comparable to that of BQ123, $pK_B$ 7.53 (95% CI 7.37-7.69).

Figure 17:
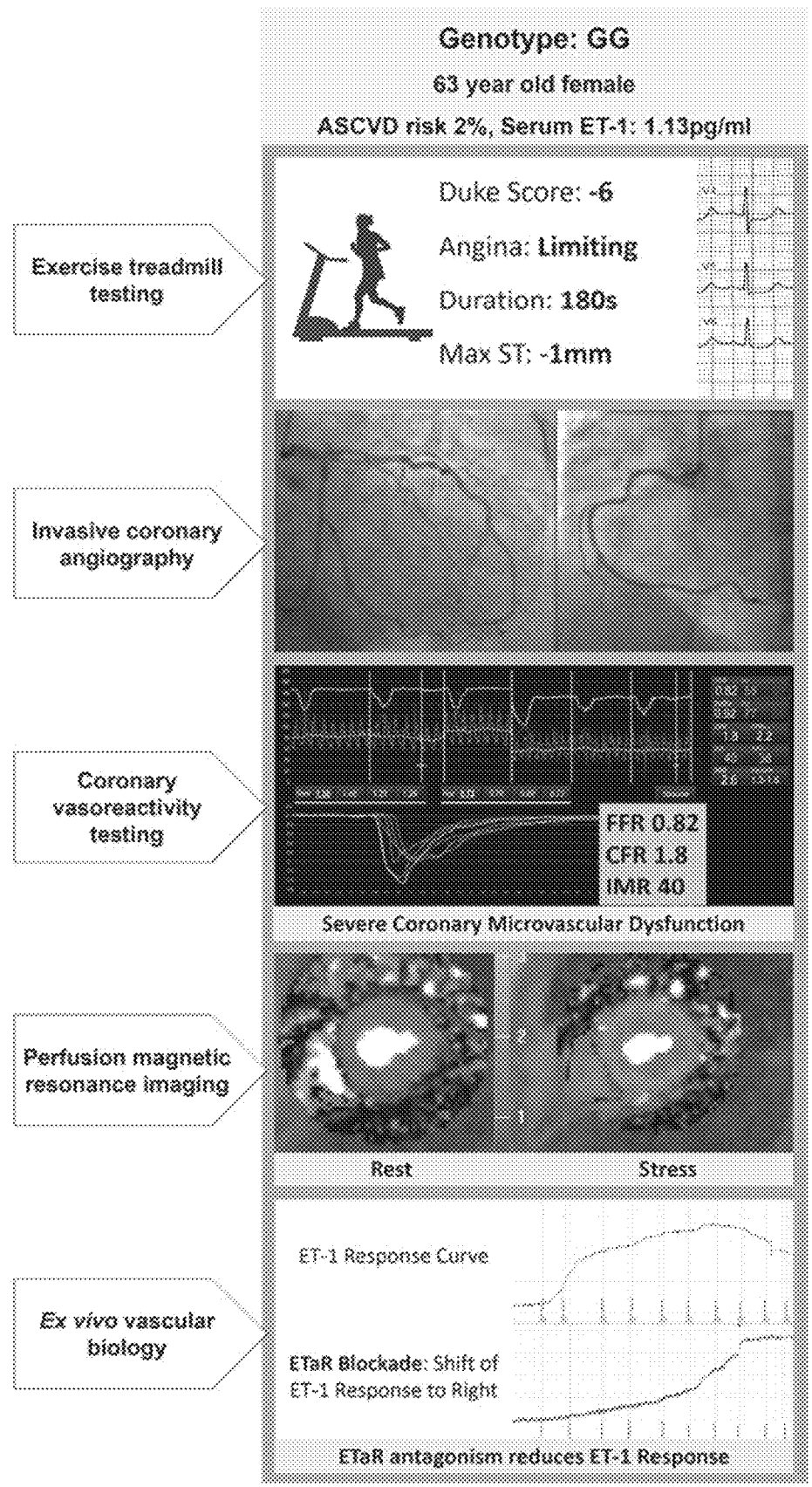
FIG. 17 GG (high-risk endothelin-1 gene enhancer). Illustrative case from a patient with stable angina including representative images from invasive and non-invasive work up are shown in relation to clinical presentation and endothelin-1 enhancer genotype. Maximum ST represents the maximum planar or down sloping ST-segment depression during the exercise treadmill test. Invasive coronary angiography of both subjects is near identical showing only minimal luminal irregularities. White arrows represent sub-endocardial inducible ischaemic myocardium during adenosine stress magnetic resonance imaging in a patient with severe coronary microvascular dysfunction. Ex vivo vascular biology (bottom panel) shows typical endothelin-1-mediated vessel constriction during wire myography. Increasing vessel tension corresponds to the rising curve at each dose titration. A paired identical vessel experiment is performed after incubation with BQ123, an $ET_A$ receptor antagonist. This curve is marked in blue, the curve of endothelin-1 response is shifted to the right indicating that the $ET_A$ receptor mediates vasoconstriction. Despite the endothelin-1 gene enhancer, the GG subject does not appear to have $ET_A$ receptor down-regulation with similar levels of antagonist potency. This supports that $ET_A$ receptor antagonism in this group of patients may have therapeutic benefit. CFR, coronary flow reserve; $ET_A$, endothelin A receptor; FFR, fractional flow reserve; IMR, index of microcirculatory resistance.

Crucially, these studies confirmed that zibotentan produced a concentration-dependent inhibition of an established constrictor response to ET-1 and was still efficacious in subjects with G allele (P<0.001; FIG. 16C). FIG. 17 shows representative investigations from a female subject with few traditional cardiovascular risk factors but high-risk ET-1 enhancer genotype (GG).

TABLE 4

Pathophysiology: vascular biology of ET-1

| | SNP(rs9349379)genotype (n544) | | | |
|---|---|---|---|---|
| | AA (N516) | AG (N5 14) | GG (N514) | P-value [a] |
| Vessel diameter (um) | 344 (±88) | 342 (±89) | 347 (±125) | 0.851 |
| Vessel length (mm) | 1.85 (±0.12) | 1.87 (±0.10) | 1.82 (±0.11) | 0.276 |
| ACh $E_{max}$ (%) | 77.7 (52.9-97.8) | 80.2 (59.9-97.6) | 92.5 (57.8-99.1) | 0.696 |
| ACh $pEC_{50}$ | 7.28 (638-7.82) | 7.26 (6.82-8.00) | 6.96 (6.84-7.44) | 0.338 |
| ET-1 Emax (%) | 122.3 (135.7-134.7) | 115.5 (107.5-125.2) | 129.7 (115.8-151.2) | 0.533 |
| ET-1 $pEC_{50}$ | 9.34 (9.15-9.52) | 9.45 (9 24-9.67) | 9.32 (896-9.69) | 0.533 |
| BQ123 $pK_B$ (±SEM) | 7.07 (±0.23) | 7.79 (±0.35) | 7.41 (±0.26) | 0.209 |

Forty-four (65%) of 68 patients who underwent invasive biopsies had a sufficient number of small arteries to undergo paired cumulative concentration response curves (CCRCs) to ET-1 in the presence and absence of an ETA receptor antagonist. Data are expressed as mean (±SD) or mean (95% CI for pooled best fit CCRC).
CCRC, cumula- tive concentration response curves were drawn with best-fit derived values.
$pK_B$ data involved paired vessels undergoing ET-1 CCRC in the presence or absence of BQ123 ETA receptor antagonist (available in 37 out of the 44 subjects: AA N = 14; AG N = 10; GG N = 13).
[a]Significance determined using ANOVA for normally distributed means, Kruskal-Wallis test used for between group comparison of non-parametric variables and extra-sum of squares F test (for CCRC pooled best fit ET-1 data).
There were no differences in between group baseline demographics in this vascular sub-study.

Discussion: We identify a novel genetic risk locus for CMD. Our study extends a report from the WISE investigators on genotype associations with arterial vasomotion.[13A] Our results support the hypothesis that dysregulation of the ET-1/$ET_A$ receptor system underpins abnormalities in the coronary microcirculation leading to myocardial ischaemia. Firstly, rs9349379-G allele status is associated with higher serum ET-1 and the presence and extent of CMD in patients with angina but without obstructive coronary disease. Secondly, the genetic polymorphism associates with ischaemia testing using distinct, non-invasive modalities including exercise stress electrocardiography and stress perfusion CMR. Thirdly, we demonstrate in ex vivo human small peripheral resistance vessels that the $ET_A$ vasoconstrictor response is not down-regulated in the presence of increases in endothelin gene expression and ET-1 activity in patients with the rs9349379-G allele. Finally, we provide proof-of-concept mechanistic data supporting a role for zibotentan, an orally active highly selective $ET_A$ receptor antagonist, in reversing established ET-1-mediated vasoconstriction. These findings have potential clinical relevance since zibotentan is available for repositioning as a novel, disease-modifying therapy in this patient population. The results of our study support the rationale for the 'Precision Medicine with Zibotentan in Microvascular Angina (PRIZE)' trial involving gene testing for the SNP rs9349379 and linked therapy (ClinicalTrials.gov Identifier: NCT04097314).

Endothelin dysregulation: Pre-clinical studies in experimental models of CMD implicate increased cardiac ET-1 production leading to endothelial dysfunction, enhanced vascular expression of rho-kinases, and reactive oxidant species such as superoxide and enhanced ET-1-mediated vasoconstriction.[38A] In patients with angina but no obstructive CAD, microvascular dysfunction is a systemic phenomenon characterized by peripheral endothelial dysfunction and enhanced peripheral small vessel vasoconstriction.[31A, 39A] Further, impaired coronary microvascular function and the propensity to myocardial ischaemia may increase longer-term risk of major adverse cardiac events.[40A,41A]

Our study is distinct and builds on our prior vascular studies of ET-1 in microvascular angina as we used zibotentan which has more potential for clinical translation requiring future phase II studies.31 In addition, subjects were analysed by ET-1 rs9349379-G allele status rather than presence or absence of CMD. We observed that chronic exposure to increased circulating concentrations of ET-1, as reflected by rs9349379-G allele status, did not lead to down-regulation to $ET_A$-mediated ET-1 vasoconstriction in patients with microvascular angina. The converse SNP (rs9349379-A) was recently found to be associated with spontaneous coronary artery dissection (SCAD) which typically occurs in patients without atherosclerosis.[21A] This finding is consistent with our work, particularly given that microvascular function is typically normal in SCAD.[42A]

We showed that rs9349379-G allele was associated with higher serum ET-1 levels which is consistent with previous studies whereby the SNP associates with higher levels of ET-1 and its precursor (Big ET-1) in healthy subjects. Interestingly, the ET-1 plasma concentration in our INOCA population is comparable to ET-1 plasma concentrations in other conditions including pulmonary artery hypertension[43A] but lower than in other INOCA cohorts.[44A] We acknowledge that abluminal secretion of ET-1 away from endothelial cells towards underlying vascular smooth muscle means circulating concentrations of ET-1 are an imperfect measure of ET-1 activity in vascular tissues.[45A] Chronic elevation of circulating ET-1 may lead to adaptive down-regulation of its endogenous G-protein coupled receptors. This phenomenon has been described for $ET_A$ receptors in mice in which the clearing $ET_B$ receptor has been knocked out.[46A] Cardiovascular risk factors, including blood pressure, were not associated with rs9349379-G allele in our population, whereas an inverse associations have been observed in much larger populations.[17A] This is particularly interesting given its association with atherogenesis and CAD. It is thought that excess ET-1 effects healthy populations mediate hypotension via hypotension via $ET_B$-induced nitric oxide and prostacyclin production, resultant vasodilation, diuresis, and natriuresis.[47A] Our study was underpowered to determine significant differences between baseline blood pressures which may also be confounded by treatment for hypertension.

Microvascular angina is a chronic, debilitating condition of unmet therapeutic need. Our vascular pharmacology findings indicate that despite a genetic predisposition to enhanced endothelin gene expression based on the rs9349379-G allele status, potentially leading to lifelong enhanced exposure to circulating concentrations of ET-1, the net effect on ET-1 response or sensitivity to $ET_A$ antagonists was similar between the groups by rs9349379 allele status. The $ET_A$ receptor may not be down-regulated in affected patients raising the potential for health gain by treatment with a selective $ET_A$ receptor antagonist, such as zibotentan. Importantly, BQ123 fully blocked the constrictor responses in all of the groups. Our vascular pharmacology study was specifically focused on the relationships between the rs9349379-Gallele status, ET-1 vasoactive responses, and $ET_A$ receptor blockade. Patients with microvascular angina may have similar tissue responses to oral $ET_A$ receptor blocker therapy—this important possibility merits further (NCT04097314).

In a mechanistic, randomized, controlled trial in patients with microvascular angina, Johnson and Gould[48A] reported that $ET_A$ receptor antagonism increased (improved) the homogeneity of resting myocardial perfusion. Their study used cardiac positron emission tomography (PET) to quantify the homogeneity index (a visual notion of homogeneity derived from PET).[49A] Kaski et al.[50A] showed that patients with microvascular angina were exposed to increased circulating concentrations of ET-1 which in turn was associated with increased coronary vascular resistance and impaired coronary blood flow. Recently, Theuerle et al.[51A] have shown that plasma ET-1 is associated with invasive CMD in a 32 INOCA patients, however, the relationship was driven by elevated microvascular resistance and not impaired CFR.

Limitations: We describe compelling mechanistic evidence for a functional SNP being linked to CMD. We have followed accepted guidelines for CMD classifications, but it is recognized there are caveats with any classification system and acknowledge these are also relevant to this study. Firstly, we adopted binary cut-offs for the IDP test. It is possible that indeterminate (grey-zone or borderline) test results may have misclassified some patients. Furthermore, patients with CMD were heterogeneous and we aggregated patients with different types of microvascular dysfunction, e.g. impaired flow reserve, increased microvascular resistance, abnormal ACh response. Nonetheless, the vascular phenotype of affected patients was of coronary vascular dysfunction based on consensus guidelines for abnormal coronary microvascular response during systemic adenosine, an abnormal vasomotor response to intracoronary ACh, or both.[64] In support of this approach, we observed a strong linear relationship between CMD and non-invasive ischaemia testing on the exercise treadmill (FIG. 15F). In addition, heterogeneity is the rule rather than exception when considering many similar cardiovascular disorders, for example heart failure with preserved ejection fraction.[52A] Our stratified sensitivity analysis by CMD type, i.e. structural microvascular disease (i.e. raised IMR) and impaired vasodilator reserve (reduced CFR) (Table 3), lend further support to the design of our translational study. Secondly, not all patients underwent treadmill exercise testing.

The tests were indicated as part of standard care and clinical, rather than core laboratory, reports were available for analysis. Nevertheless, they were performed according to the Bruce protocol and the results were determined in a standardized manner, blinded to rs9349379 allele status. Treadmill exercise testing is an imperfect measure of ischaemia and hence it is plausible that the known association of the rs9349379-G allele with epicardial CAD is a confounding factor. Gould and Johnson[53A] recently highlighted how flush ostial branch vessel occlusion may account for ischaemia despite a visual 'normal' angiogram without stenosis. On the other hand, the DTS has a mature associated literature with proven utility in CMD patients.[54A,55A] The relatively small sample size and possibility of unmeasured baseline differences increases the possibility of Type I error. Thirdly, we administered intra-arterial doses of short acting GTN (100-200 µg) to facilitate procedure safety relating to transradial access, coronary arteriography, and invasive coronary vasoreactivity testing. Theoretically, GTN may affect the vascular responses to ACh; however, the half-life of GTN is around 2 min. Hence, after 10 min, only 3% of the GTN dose is bioavailable and we think the potential for confounding and a false negative test for microvascular vasospasm is unlikely.

Conversely, a positive ACh test confounds assessment of true resting flow and may lead to falsely lowered CFR and hence we support ACh testing after adenosine assessment. Finally, we compared the allele prevalence within our cohort from Scotland with a pooled multicentre contemporary medical genome reference group of controls. Our study would have been strengthened by a control comparator group from the same area and ethnic background as our subjects. Further, although the SNP did not fulfil the Hardy-Weinberg equilibrium for the population as a whole, the control group from this study without CMD was consistent with the equilibrium ($x^2$ 2.99, P=0.084). It is plausible that HW was not met in the CMD group due to its association with the rs9349379-G allele of interest. This study is a cross-sectional analysis of a single genetic locus and provides associative findings of clinical interest but may overlook other important genetic risk determinants.

Clinical translation: These observations hypothesis generating particularly given the small sample size and heterogeneous patient population. The findings require external validation in other CMD cohorts whilst future work in populations from different regions would provide helpful context. Overall, our study supports the case for selective $ET_A$ blockade distinct from $ET_B$ modulation in patients with microvascular disease in the heart. Oral $ET_A$-selective blockade has therapeutic potential by attenuating the propensity to microvascular vasospasm, increasing coronary blood flow, and further improving coronary endothelial function through NO-mediated release.[56A] Zibotentan is one compound that holds promise as the most $ET_A$ selective of all orally active $ET_A$ receptor antagonists, which makes it particularly suited to use in microvascular angina. A targeted approach using selective $ET_A$ receptor antagonist therapy in patients based on genotype is being assessed in the PRIZE trial (NCT04097314).

Conclusion: We identified a genetic risk locus for CMD. The common genetic polymorphism (SNP rs9349379-G allele) was associated with higher ET-1 and both invasive CMD and non-invasive tests for ischaemia in subjects with angina but no obstructive CAD. Mechanistic ex vivo studies confirmed subjects with this functional allele have preserved response to $ET_A$ receptor blockade. Zibotentan, an orally active $ET_A$ receptor antagonist, reversed an established ET-1-mediated vasoconstriction. This study offers hope for angina patients although future trials are needed to determine whether CMD represents a potential new disease subtype for $ET_A$ antagonist therapy.

REFERENCES

A number of publications are cited above in order to more fully describe and disclose the invention and the state of the art to which the invention pertains. Full citations for these references are provided below. The entirety of each of these references is incorporated herein.

Numbered References (Except for Example 5)

1. Global, regional, and national age-sex specific all-cause and cause-specific mortality for 240 causes of death, 1990-2013: a systematic analysis for the Global Burden of Disease Study 2013. *The Lancet* 2015; 385(9963): 117-71.
2. Cardiovascular Disease Statistics 2018. London: British Heart Foundation; 2018.
3. Bairey Merz C N, Pepine C J, Walsh M N, Fleg J L. Ischemia and No Obstructive Coronary Artery Disease (INOCA): Developing Evidence-Based Therapies and Research Agenda for the Next Decade. *Circulation* 2017; 135(11): 1075-92.
4. Ong P, Camici P G, Beltrame J F, et al. International standardization of diagnostic criteria for microvascular angina. *Int J Cardiol* 2018; 250: 16-20.
5. Taqueti V R, Shaw L J, Cook N R, et al. Excess Cardiovascular Risk in Women Relative to Men Referred for Coronary Angiography Is Associated With Severely Impaired Coronary Flow Reserve, Not Obstructive Disease. *Circulation* 2017; 135(6): 566-77.
6. Pepine C J, Anderson R D, Sharaf B L, et al. Coronary microvascular reactivity to adenosine predicts adverse outcome in women evaluated for suspected ischemia results from the National Heart, Lung and Blood Institute WISE (Women's Ischemia Syndrome Evaluation) study. *J Am Coll Cardiol* 2010; 55(25): 2825-32.
7. Ford T J, Stanley B, Good R, et al. Stratified Medical Therapy Using Invasive Coronary Function Testing In Angina: CorMicA Trial. *J Am Coll Cardiol* 2018.
8. Phan A, Shufelt C, Merz C N. Persistent chest pain and no obstructive coronary artery disease. *JAMA* 2009; 301(14): 1468-74.
9. Jespersen L, Hvelplund A, Abildstrom S Z, et al. Stable angina pectoris with no obstructive coronary artery disease is associated with increased risks of major adverse cardiovascular events. *Eur Heart J* 2012; 33(6): 734-44.
10. Jordan K P, Timmis A, Croft P, et al. Prognosis of undiagnosed chest pain: linked electronic health record cohort study. *BMJ* 2017; 357: j1194.
11. Hsu L-Y, Jacobs M, Benovoy M, et al. Diagnostic Performance of Fully Automated Pixel-Wise Quantitative Myocardial Perfusion Imaging by Cardiovascular Magnetic Resonance. *JACC Cardiovasc Imaging* 2018.
12. Wang X, Nie S-P. The coronary slow flow phenomenon: characteristics, mechanisms and implications. *Cardiovascular Diagnosis and Therapy*; Vol 1, No 1 (December 2011): *Cardiovascular Diagnosis and Therapy* 2011.
13. Kaski J C, Elliott P M, Salomone O, et al. Concentration of circulating plasma endothelin in patients with angina and normal coronary angiograms. *Br Heart J* 1995; 74(6): 620-4.
14. Piatti P, Fragasso G, Monti L D, et al. Endothelial and metabolic characteristics of patients with angina and angiographically normal coronary arteries. *J Am Coll Cardiol* 1999; 34(5): 1452-60.
15. Winkles J A, Alberts G F, Brogi E, Libby P. Endothelin-1 and endothelin receptor mRNA expression in normal and atherosclerotic human arteries. *Biochem Biophys Res Commun* 1993; 191(3): 1081-8.
16. Reriani M, Raichlin E, Prasad A, et al. Long-term administration of endothelin receptor antagonist improves coronary endothelial function in patients with early atherosclerosis. *Circulation* 2010; 122(10): 958-66.
17. Zile M R, Bourge R C, Redfield M M, Zhou D, Baicu C F, Little W C. Randomized, double-blind, placebo-controlled study of sitaxsentan to improve impaired exercise tolerance in patients with heart failure and a preserved ejection fraction. *JACC Heart Fail* 2014; 2(2): 123-30.
18. Maguire J J, Davenport A P. Endothelin©25—new agonists, antagonists, inhibitors and emerging research frontiers: IUPHAR Review 12. *Br J Pharmacol* 2014; 171(24): 5555-72.
19. Ford T J, Corcoran D, Oldroyd K G, et al. Rationale and design of the British Heart Foundation (BHF) Coronary Microvascular Angina (CorMicA) stratified medicine clinical trial. *Am Heart J* 2018; 201: 86-94.
20. De Bruyne B, Baudhuin T, Melin J A, et al. Coronary flow reserve calculated from pressure measurements in humans. Validation with positron emission tomography. *Circulation* 1994; 89(3): 1013-22.
21. Pijls N H J. Coronary Thermodilution to Assess Flow Reserve: Validation in Humans. *Circulation* 2002; 105 (21): 2482-6.
22. Fearon W F, Balsam L B, Farouque H M, et al. Novel index for invasively assessing the coronary microcirculation. *Circulation* 2003; 107(25): 3129-32.
23. Lerman A, Holmes D R, Bell M R, Garratt K N, Nishimura R A, Burnett J C. Endothelin in Coronary Endothelial Dysfunction and Early Atherosclerosis in Humans. *Circulation* 1995; 92(9): 2426-31.
24. Ford T J, Rocchiccioli P, Good R, et al. Systemic microvascular dysfunction in microvascular and vasospastic angina. *Eur Heart J* 2018; [Epub ahead of print].
25. Gupta R M, Hadaya J, Trehan A, et al. A Genetic Variant Associated with Five Vascular Diseases Is a Distal Regulator of Endothelin-1 Gene Expression. *Cell* 2017; 170(3): 522-33 e15.
26. Maguire J J, Davenport A P. ETA receptor-mediated constrictor responses to endothelin peptides in human blood vessels in vitro. *Br J Pharmacol* 1995; 115(1): 191-7.

Numbered References for Example 5

1A. Likoff W, Segal B L, Kasparian H. Paradox of normal selective coronary arteriograms in patients considered to have unmistakable coronary heart disease. *N Engl J Med* 1967; 276:1063-1066.
2A. Shah S J, Lam C S P, Svedlund S, Saraste A, Hage C, Tan R-S, Beussink-Nelson L, Ljung Faxén U, Fermer M L, Broberg M A, Gan L-M, Lund L H. Prevalence and correlates of coronary microvascular dysfunction in heart failure with preserved ejection fraction: PROMIS-HFpEF. *Eur Heart J* 2018; 39:3439-3450.
3A. Mohandas R, Segal M S, Huo T, Handberg E M, Petersen J W, Johnson B D, Sopko G, Bairey Merz C N, Pepine C J. Renal function and coronary microvascular dysfunction in women with symptoms/signs of ischemia. *PLoS One* 2015; 10: e0125374.
4A. Singh A, Greenwood J P, Berry C, Dawson D K, Hogrefe K, Kelly D J, Dhakshinamurthy V, Lang C C, Khoo J P, Sprigings D, Steeds R P, Jerosch-Herold M, Neubauer S, Prendergast B, Williams B, Zhang R, Hudson I, Squire I B, Ford I, Samani N J, McCann G P. Comparison of exercise testing and CMR measured myocardial perfusion reserve for predicting outcome in asymptomatic aortic stenosis: the PRognostic Importance of MIcrovascular Dysfunction in Aortic Stenosis (PRIMID AS) Study. *Eur Heart J* 2017; 38:1222-1229.
5A. Bajaj N S, Osborne M T, Gupta A, Tavakkoli A, Bravo P E, Vita T, Bibbo C F, Hainer J, Dorbala S, Blankstein R, Bhatt D L, Di Carli M F, Taqueti V R. Coronary microvascular dysfunction and cardiovascular risk in obese patients. *J Am Coll Cardiol* 2018; 72:707-717.

6A. Ong P, Camici P G, Beltrame J F, Crea F, Shimokawa H, Sechtem U, Kaski J C, Bairey Merz C N; Coronary Vasomotion Disorders International Study Group (COVADIS). International standardization of diagnostic criteria for microvascular angina. Int J Cardiol 2018; 250: 16-20.

7A. Patel M R, Peterson E D, Dai D, Brennan J M, Redberg R F, Anderson H V, Brindis R G, Douglas P S. Low diagnostic yield of elective coronary angiography. N Engl J Med 2010; 362:886-895.

8A. Ford T J, Stanley B, Good R, Rocchiccioli P, McEntegart M, Watkins S, Eteiba H, Shaukat A, Lindsay M, Robertson K, Hood S, McGeoch R, McDade R, Yii E, Sidik N, McCartney P, Corcoran D, Collison D, Rush C, McConnachie A, Touyz R M, Oldroyd K G, Berry C. Stratified medical therapy using invasive coronary function testing in angina: the CorMicA trial. J Am Coll Cardiol 2018; 72:2841-2855.

9A. Sara J D, Widmer R J, Matsuzawa Y, Lennon R J, Lerman L O, Lerman A. Prevalence of coronary microvascular dysfunction among patients with chest pain and nonobstructive coronary artery disease. JACC Cardiovasc Interv 2015; 8:1445-1453.

10A. Ong P, Athanasiadis A, Borgulya G, Vokshi I, Bastiaenen R, Kubik S, Hill S, Schaufele T, Mahrholdt H, Kaski J C, Sechtem U. Clinical usefulness, angiographic characteristics, and safety evaluation of intracoronary acetylcholine provocation testing among 921 consecutive white patients with unobstructed coronary arteries. Circulation 2014; 129:1723-1730.

11A. Taqueti V R, Shaw L J, Cook N R, Murthy V L, Shah N R, Foster C R, Hainer J, Blankstein R, Dorbala S, Di Carli M F. Excess cardiovascular risk in women relative to men referred for coronary angiography is associated with severely impaired coronary flow reserve, not obstructive disease. Circulation 2017; 135: 566-577.

12A. Bairey Merz C N, Shaw L J, Reis S E, Bittner V, Kelsey S F, Olson M, Johnson B D, Pepine C J, Mankad S, Sharaf B L, Rogers W J, Pohost G M, Lerman A, Quyyumi A A, Sopko G, Investigators W. Insights from the NHLBI-Sponsored Womenis Ischemia Syndrome Evaluation (WISE) study: part II: gender differences in presentation, diagnosis, and outcome with regard to gender-based pathophysiology of atherosclerosis and macrovascular and microvascular coronary disease. J Am Coll Cardiol 2006; 47(3 Suppl):521-529.

13A. Pacheco Claudio C, Quesada O, Pepine C J, Noel Bairey Merz C. Why names matter for women: MINOCA/INOCA (myocardial infarction/ischemia and no obstructive coronary artery disease). Clin Cardiol 2018; 41:185-193.

14A. Halcox J P, Nour K R, Zalos G, Quyyumi A A. Endogenous endothelin in human coronary vascular function: differential contribution of endothelin receptor types A and B. Hypertension 2007; 49:1134-1141.

15A. Lanza G A, Crea F. Primary coronary microvascular dysfunction: clinical presentation, pathophysiology, and management. Circulation 2010; 121:2317-2325.

16A. Pekdemir H, Polat G, Cin V G, Camsari A, Cicek D, Akkus M N, Doyen O, Katircibasi M T, Muslu N. Elevated plasma endothelin-1 levels in coronary sinus during rapid right atrial pacing in patients with slow coronary flow. Int J Cardiol 2004; 97:35-41.

17A. Gupta R M, Hadaya J, Trehan A, Zekavat S M, Roselli C, Klarin D, Emdin C A, Hilvering C R E, Bianchi V, Mueller C, Khera A V, Ryan R J H, Engreitz J M, Issner R, Shoresh N, Epstein C B, de Laat W, Brown J D, Schnabel R B, Bernstein B E, Kathiresan S. A genetic variant associated with five vascular diseases is a distal regulator of endothelin-1 gene expression. Cell 2017; 170:522-533.e15.

18A. The CDC, Nikpay M, Goel A, Won H-H, Hall L M, Willenborg C, Kanoni S, Saleheen D, Kyriakou T, Nelson C P, Hopewell J C, Webb T R, Zeng L, Dehghan A, Alver M, Armasu S M, Auro K, Bjonnes A, Chasman D I, Chen S, Ford I, Franceschini N, Gieger C, Grace C, Gustafsson S, Huang J, Hwang S-J, Kim Y K, Kleber M E, Lau K W, Lu X, Lu Y, Lyytika®inen L-P, Mihailov E, Morrison A C, Pervjakova N, Qu L, Rose L M, Salfati E, Saxena R, Scholz M, Smith A V, Tikkanen E, Uitterlinden A, Yang X, Zhang W, Zhao W, de Andrade M, de Vries P S, van Zuydam N R, Anand S S, Bertram L, Beutner F, Dedoussis G, Frossard P, Gauguier D, Goodall A H, Gottesman O, Haber M, Han B-G, Huang J, Jalilzadeh S, Kessler T, König I R, Lannfelt L, Lieb W, Lind L, Lindgren C M, Lokki M-L, Magnusson P K, Mallick N H, Mehra N, Meitinger T, Memon F-U-R, Morris A P, Nieminen M S, Pedersen N L, Peters A, Rallidis L S, Rasheed A, Samuel M, Shah S H, Sinisalo J, Stirrups K E, Trompet S, Wang L, Zaman K S, Ardissino D, Boerwinkle E, Borecki I B, Bottinger E P, Buring J E, Chambers J C, Collins R, Cupples L A, Danesh J, Demuth I, Elosua R, Epstein S E, Esko T, Feitosa M F, Franco O H, Franzosi M G, Granger C B, Gu D, Gudnason V, Hall A S, Hamsten A, Harris T B, Hazen S L, Hengstenberg C, Hofman A, Ingelsson E, Iribarren C, Jukema J W, Karhunen P J, Kim B-J, Kooner J S, Kullo I J, Lehtima®ki T, Loos R J F, Melander O, Metspalu A, Ma®rz W, Palmer C N, Perola M, Quertermous T, Rader D J, Ridker P M, Ripatti S, Roberts R, Salomaa V, Sanghera D K, Schwartz S M, Seedorf U, Stewart A F, Stott D J, Thiery J, Zalloua P A, OiDonnell C J, Reilly M P, Assimes T L, Thompson J R, Erdmann J, Clarke R, Watkins H, Kathiresan S, McPherson R, Deloukas P, Schunkert H, Samani N J, Farrall M. A comprehensive 1,000 Genomes-based genome-wide association meta-analysis of coronary artery disease. Nat Genet 2015; 47:1121.

19A. Ford T J, Corcoran D, Oldroyd K G, McEntegart M, Rocchiccioli P, Watkins S, Brooksbank K, Padmanabhan S, Sattar N, Briggs A, McConnachie A, Touyz R, Berry C. Rationale and design of the British Heart Foundation (BHF) Coronary Genetic dysregulation of ET-1 and microvascular dysfunction 13 Microvascular Angina (CorMicA) stratified medicine clinical trial. Am Heart J 2018; 201:86-94.

20A. Rose G, McCartney P, Reid D D. Self-administration of a questionnaire on chest pain and intermittent claudication. Br J Prev Soc Med 1977; 31:42-48.

21A. Adlam D, Olson $T_M$, Combaret N, Kovacic J C, Iismaa SE, Al-Hussaini A, OiByrne M M, Bouajila S, Georges A, Mishra K, Braund P S, diEscamard V, Huang S, Margaritis M, Nelson C P, de Andrade M, Kadian-Dodov D, Welch C A, Mazurkiewicz S, Jeunemaitre X, Wong C M Y, Giannoulatou E, Sweeting M, Muller D, Wood A, McGrath-Cadell L, Fatkin D, Dunwoodie S L, Harvey R, Holloway C, Empana J-P, Jouven X, CARDloGRAMPlusC4D Study Group Olin J W, Gulati R, Tweet M S, Hayes S N, Samani N J, Graham R M, Motreff P, Bouatia-Naji N. Association of the PHACTR1/EDN1 genetic locus with spontaneous coronary artery dissection. J Am Coll Cardiol 2019; 73:58-66.

22A. Beltrame J F, Crea F, Kaski J C, Ogawa H, Ong P, Sechtem U, Shimokawa H B, Merz, C N; Coronary Vasomotion Disorders International Study Group (CO- 23A. Ford T J, Stanley B, Good R, Rocchiccioli P, McEntegart M, Watkins S, Eteiba H, Shaukat A, Lindsay M, Robertson K, Hood S, McGeoch R, McDade R, Yii E, Sidik N, McCartney P, Corcoran D, Collison D, Rush C, McConnachie A, Touyz R M, Oldroyd K G, Berry C. Stratified medical therapy using invasive coronary function testing in angina: CorMicA Trial. *J Am Coll Cardiol* 2018; 72:2841-2855.

24A. De Bruyne B, Baudhuin T, Melin J A, Pijls N H, Sys S U, Bol A, Paulus W J, Heyndrickx G R, Wijns W. Coronary flow reserve calculated from pressure measurements in humans. Validation with positron emission tomography. *Circulation* 1994; 89:1013-1022.

25A. Pijls N H J, De Bruyne B, Smith L, Aarnoudse W, Barbato E, Bartunek J, Bech G J W, Van De Vosse F. Coronary thermodilution to assess flow reserve: validation in humans. *Circulation* 2002; 105:2482-486.

26A. Murthy V L, Naya M, *Taqueti* VR, Foster C R, Gaber M, Hainer J, Dorbala S, Blankstein R, Rimoldi O, Camici P G, Di Carli M F. Effects of sex on coronary microvascular dysfunction and cardiac outcomes. *Circulation* 2014; 129: 2518-2527.

27A. Fearon W F, Balsam L B, Farouque H M, Caffarelli A D, Robbins R C, Fitzgerald P J, Yock P G, Yeung A C. Novel index for invasively assessing the coronary microcirculation. *Circulation* 2003; 107:3129-3132.

28A. Lee B K, Lim H S, Fearon W F, Yong A S, Yamada R, Tanaka S, Lee D P, Yeung A C, Tremmel J A. Invasive evaluation of patients with angina in the absence of obstructive coronary artery disease. *Circulation* 2015; 131:1054-1060.

29A. Lerman A, Holmes D R, Bell M R, Garratt K N, Nishimura R A, Burnett J C. Endothelin in coronary endothelial dysfunction and early atherosclerosis in humans. *Circulation* 1995; 92:2426-2431.

30A. Ohba K, Sugiyama S, Sumida H, Nozaki T, Matsubara J, Matsuzawa Y, Konishi M, Akiyama E, Kurokawa H, Maeda H, Sugamura K, Nagayoshi Y, Morihisa K, Sakamoto K, Tsujita K, Yamamoto E, Yamamuro M, Kojima S, Kaikita K, Tayama S, Hokimoto S, Matsui K, Sakamoto T, Ogawa H. Microvascular coronary artery spasm presents distinctive clinical features with endothelial dysfunction as nonobstructive coronary artery disease. *J Am Heart Assoc* 2012; 1:e002485.

31A. Ford T J, Rocchiccioli P, Good R, McEntegart M, Eteiba H, Watkins S, Shaukat A, Lindsay M, Robertson K, Hood S, Yii E, Sidik N, Harvey A, Montezano A C, Beattie E, Haddow L, Oldroyd K G, Touyz R M, Berry C. Systemic microvascular dysfunction in microvascular and vasospastic angina. *Eur Heart J* 2018; 39: 4086-4097.

32A. Cerqueira M D, Weissman N J, Dilsizian V, Jacobs A K, Kaul S, Laskey W K, Pennell D J, Rumberger J A, Ryan T, Verani M S; American Heart Association Writing Group on Myocardial Segmentation and Registration for Cardiac Imaging. Standardized myocardial segmentation and nomenclature for tomographic imaging of the heart. A statement for healthcare professionals from the Cardiac Imaging Committee of the Council on Clinical Cardiology of the American Heart Association. *Circulation* 2002; 105:539-542.

33A. Schulz-Menger J, Bluemke D A, Bremerich J, Flamm S D, Fogel M A, Friedrich M G, Kim R J, von Knobelsdorff-Brenkenhoff F, Kramer C M, Pennell D J, Plein S, Nagel E. Standardized image interpretation and post processing in cardiovascular magnetic resonance: society for Cardiovascular Magnetic Resonance (SCMR) board of trustees task force on standardized post processing. *J Cardiovasc Magn Reson* 2013; 15:35.

34A. Hsu L-Y, Jacobs M, Benovoy M, Ta A D, Conn H M, Winkler S, Greve A M, Chen M Y, Shanbhag S M, Bandettini W P, Arai A E. Diagnostic performance of fully automated pixel-wise quantitative myocardial perfusion imaging by cardiovascular magnetic resonance. *JACC Cardiovasc Imaging* 2018; 11:697-707.

35A. Shaw L J, Peterson E D, Shaw L K, Kesler K L, DeLong E R, Harrell F E Jr, Muhlbaier L H, Mark D B. Use of a prognostic treadmill score in identifying diagnostic coronary disease subgroups. *Circulation* 1998; 98:1622-1630.

36A. Mark D B, Shaw L, Harrell F E Jr, Hlatky M A, Lee K L, Bengtson J R, McCants C B, Califf R M, Pryor D B. Prognostic value of a treadmill exercise score in outpatients with suspected coronary artery disease. *N Engl J Med* 1991; 325:849-853.

37A. Woodward M, Brindle P, Tunstall-Pedoe H. Adding social deprivation and family history to cardiovascular risk assessment: the ASSIGN score from the Scottish Heart Health Extended Cohort (SHHEC). *Heart* 2005; 93:172-176.

38A. Tsai S H, Lu G, Xu X, Ren Y, Hein T W, Kuo L. Enhanced endothelin-1/Rhokinase signalling and coronary microvascular dysfunction in hypertensive myocardial hypertrophy. *Cardiovasc Res* 2017; 113:1329-1337.

39A. Jaarsma C, Vink H, van Haare J, Bekkers S, van Rooijen B D, Backes W H, Wildberger J E, Crijns H J, van Teeffelen J, Schalla S. Non-invasive assessment of microvascular dysfunction in patients with microvascular angina. *Int J Cardiol* 2017; 248:433-439.

40A. Suda A, Takahashi J, Hao K, Kikuchi Y, Shindo T, Ikeda S, Sato K, Sugisawa J, Matsumoto Y, Miyata S, Sakata Y, Shimokawa H. Coronary functional abnormalities in patients with angina and nonobstructive coronary artery disease. *J Am Coll Cardiol* 2019; 74:2350-2360.

41A. Ford T J, Berry C, De Bruyne B, Yong A S C, Barlis P, Fearon W F, Ng M. Physiological predictors of acute coronary syndromes: emerging insights from the plaque to the vulnerable patient. *JACC Cardiovasc Interv* 2017; 10:2539-2547.

42A. Waterbury $T_M$, Tweet M S, Hayes S N, Prasad A, Lerman A, Gulati R. Coronary endothelial function and spontaneous coronary artery dissection. *Eur Heart J 95 Acute Cardiovasc Care* 2018; doi:10.1177/ 2048872618795255.

43A. Jankowich M D, Wu W C, Choudhary G. Association of elevated plasma endothelin-1 levels with pulmonary hypertension, mortality, and heart failure in African American Individuals: the Jackson Heart Study. *JAMA Cardiol* 2016; 1: 461-469.

44A. Kaski J C, Elliott P M, Salomone O, Dickinson K, Gordon D, Hann C, Holt D W. Concentration of circulating plasma endothelin in patients with angina and normal coronary angiograms. *Br Heart J* 1995; 74:620-624.

45A. Davenport A P, Hyndman K A, Dhaun N, Southan C, Kohan D E, Pollock J S, Pollock D M, Webb D J, Maguire J J. Endothelin. *Pharmacol Rev* 2016; 68:357-418.

46A. Kuc R E, Maguire J J, Davenport A P. Quantification of endothelin receptor subtypes in peripheral tissues reveals downregulation of ET(A) receptors in ET(B)-deficient mice. *Exp Biol Med (Maywood)* 2006; 231:741-745.

47A. Miller E, Czopek A, Duthie K M, Kirkby N S, van de Putte E E, Christen S, Kimmitt R A, Moorhouse R, Castellan R F, Kotelevtsev Y V, Kuc R E, Davenport A P, Dhaun N, Webb D J, Hadoke P W. Smooth muscle endothelin B receptors regulate blood pressure but not vascular function or neointimal remodeling. *Hypertension* 2017; 69:275-285.

48A. Johnson N P, Gould K L. Physiology of endothelin in producing myocardial perfusion heterogeneity: a mechanistic study using Darusentan and positron emission tomography. *J Nucl Cardiol* 2013; 20:835-844.

49A. Johnson N P, Gould K L. Clinical evaluation of a new concept: resting myocardial perfusion heterogeneity quantified by Markovian analysis of PET identifies coronary microvascular dysfunction and early atherosclerosis in 1,034 subjects. *J Nucl Med* 2005; 46:1427-1437.

50A. Cox I D, Bøtker H E, Bagger J P, Sonne H S, Kristensen B O, Kaski J C. Elevated endothelin concentrations are associated with reduced coronary vasomotor responses in patients with chest pain and normal coronary arteriograms. *J Am Coll Cardiol* 1999; 34:455-460.

51A. Theuerle J, Farouque O, Vasanthakumar S, Patel S K, Burrell L M, Clark D J, AI-125 Fiadh A H. Plasma endothelin-1 and adrenomedullin are associated with coronary artery function and cardiovascular outcomes in humans. *Int J Cardiol* 2019; 291:168-172.

52A. Kitzman D W, Upadhya B. Heart failure with preserved ejection fraction: a heterogenous disorder with multifactorial pathophysiology. *J Am Coll Cardiol* 2014; 63:457-459.

53A. Gould K L, Johnson N P. Coronary physiology beyond coronary flow reserve in microvascular angina: JACC state-of-the-art review. *J Am Coll Cardiol* 2018; 72:2642-2662.

54A. Alexander K P, Shaw L J, DeLong E R, Mark D B, Peterson E D. Value of exercise treadmill testing in women. *J Am Coll Cardiol* 1998; 32:1657-1664.

55A. Youn H J, Park C S, Moon K W, Oh Y S, Chung W S, Kim J H, Choi K B, Hong S J. Relation between Duke treadmill score and coronary flow reserve using transesophageal Doppler echocardiography in patients with microvascular angina. *Int J Cardiol* 2005; 98:403-408.

56A. Wenzel R R, Fleisch M, Shaw S, Noll G, Kaufmann U, Schmitt R, Jones C R, Clozel M, Meier B, Lüscher TF. Hemodynamic and coronary effects of the endothelin antagonist bosentan in patients with coronary artery disease. *Circulation* 1998; 98:2235-2240.

For standard molecular biology techniques, see Sambrook, J., Russel, D. W. *Molecular Cloning, A Laboratory Manual.* 3 ed. 2001, Cold Spring Harbor, New York: Cold Spring Harbor Laboratory Press.

The invention claimed is:

1. A method of treating angina in a patient with INOCA, the method comprising administering zibotentan to the patient.

2. The method of claim 1, wherein the INOCA is microvascular angina.

3. The method of claim 1, wherein the patient has been selected for treatment by measuring the index of microvascular resistance (IMR), coronary flow reserve (CFR), resistance reserve ratio (RRR), or acetylcholine (Ach) vasoreactivity in the heart of the patient, using a diagnostic guidewire in combination with pharmacological probes.

4. The method of claim 1, wherein the patient has been selected for treatment using stress perfusion MRI to quantify/diagnose the presence of coronary microvascular dysfunction in the heart of the patient.

5. The method of claim 1, wherein the patient has been selected for treatment via a method comprising the detection of the rs9349379 locus in the genome of the patient.

6. The method of claim 5, wherein the rs9349379 locus is homozygous or heterozygous for the G allele.

7. The method of claim 1, wherein the mean exercise duration of the patient, measured on a standardised treadmill test, is increased following treatment.

8. The method of claim 1, wherein the severity of the angina is reduced such that the angina is considered to fall in a lower class on the CCS angina grading scale.

* * * * *